US011092597B2

(12) United States Patent
Roman et al.

(10) Patent No.: US 11,092,597 B2
(45) Date of Patent: Aug. 17, 2021

(54) DEVICES AND METHODS FOR ANALYZING INTACT PROTEINS, ANTIBODIES, ANTIBODY SUBUNITS, AND ANTIBODY DRUG CONJUGATES

(71) Applicant: Waters Technologies Corporation, Milford, MA (US)

(72) Inventors: Gregory T. Roman, North Scituate, RI (US); James P. Murphy, Franklin, MA (US)

(73) Assignee: WATERS TECHNOLIGIES CORPORATION, Milford, MA (US)

( * ) Notice: Subject to any disclaimer, the term of this patent is extended or adjusted under 35 U.S.C. 154(b) by 455 days.

(21) Appl. No.: 15/905,935

(22) Filed: Feb. 27, 2018

(65) Prior Publication Data

US 2018/0246087 A1      Aug. 30, 2018

Related U.S. Application Data

(60) Provisional application No. 62/464,682, filed on Feb. 28, 2017.

(51) Int. Cl.
G01N 33/68    (2006.01)
G01N 33/543   (2006.01)
G01N 21/33    (2006.01)

(52) U.S. Cl.
CPC ....... *G01N 33/54346* (2013.01); *G01N 21/33* (2013.01); *G01N 33/6848* (2013.01); *G01N 33/6851* (2013.01)

(58) Field of Classification Search
None
See application file for complete search history.

(56) References Cited

U.S. PATENT DOCUMENTS

| | | | | |
|---|---|---|---|---|
| 4,567,780 | A * | 2/1986 | Oppenlander | B01L 3/0224 422/525 |
| 5,726,293 | A * | 3/1998 | Seed | C07K 14/70564 530/387.1 |
| 2009/0215185 | A1* | 8/2009 | Wang | C07F 9/6506 436/86 |
| 2009/0286258 | A1 | 11/2009 | Kaur et al. | |
| 2010/0022615 | A1* | 1/2010 | Fegley | C07D 207/36 514/425 |
| 2015/0255261 | A1 | 9/2015 | Stephenson, Jr. et al. | |
| 2017/0131245 | A1* | 5/2017 | Stoll | G01N 30/32 |

FOREIGN PATENT DOCUMENTS

| | | |
|---|---|---|
| WO | 2003054549 A2 | 7/2003 |
| WO | 2014121031 A1 | 8/2014 |

OTHER PUBLICATIONS

Aebersold R. et al. "Mass spectrometry-based proteomics." Nature. Mar. 13, 2003;422(6928):198-207.
Beck A. et al. "Characterization of therapeutic antibodies and related products." Anal Chem. Jan. 15, 2013;85(2):715-36. doi: 10.1021/ac3032355. Epub Dec. 14, 2012.
Benesch JL. et al. "Mass spectrometry of macromolecular assemblies: preservation and dissociation." Curr Opin Struct Biol. Apr. 2006;16(2):245-51. Epub Mar. 24, 2006.
Clement RE. et al. "Environmental analysis." Anal Chem. Jun. 15, 2001;73(12):2761-90.
Compton PD. et al. "On the scalability and requirements of whole protein mass spectrometry." Anal Chem. Sep. 1, 2011;83(17):6868-74. doi: 10.1021/ac2010795. Epub Jul. 29, 2011.
Fekete S. et al. "Chromatographic, Electrophoretic, and Mass Spectrometric Methods for the Analytical characterization of Protein Biopharmaceuticals." Anal Chem. Jan. 5, 2016;88(1):480-507. doi: 10.1021/acs.analchem.5b04561. Epub Dec. 16, 2015.
Fenn JB, Mann M, Meng CK, Wong SF, Whitehouse CM, Science, 1989, Science, 246, 64-71.
Heck AJ et al. "Investigation of intact protein complexes by mass spectrometry." Mass Spectrom Rev. Sep.-Oct. 2004;23(5):368-89.
Huang Y et al. "Improved liquid chromatography-MS/MS of heparan sulfate oligosaccharides via chip-based pulsed makeup flow." Anal Chem. Nov. 1, 2011;83(21):8222-9. doi: 10.1021/ac201964n. Epub Oct. 7, 2011.
Iavarone AT. et al. "Mechanism of charging and supercharging molecules in electrospray ionization." J Am Chem Soc. Feb. 26, 2003;125(8):2319-27.
Iavarone AT. et al. "Supercharged protein and peptide ions formed by electrospray ionization." Anal Chem. Apr. 1, 2001;73(7):1455-60.
Kebarle P. et al. "Electrospray: from ions in solution to ions in the gas phase, what we know now." Mass Spectrom Rev. Nov.-Dec. 2009;28(6):898-917. doi: 10.1002/mas.20247.
Leney AC et al. "Native Mass Spectrometry: What is in the Name?" J Am Soc Mass Spectrom. Jan. 2017;28(1):5-13. doi: 10.1007/s13361-016-1545-3. Epub Dec. 1, 2016.
Limbach, P. A. et al., "Experimental determination of the number of trapped ions, detection limit, and dynamic range in Fourier transform ion cyclotron resonance mass spectrometry" A. G. Anal. Chem. 1993, 65, 135-140.
Marcoux J. et al. "Native mass spectrometry and ion mobility characterization of trastuzumab emtansine, a lysine-linked15 antibody drug conjugate." Protein Sci. Aug. 2015;24(8):1210-23. doi: 10.1002/pro.2666. Epub Mar. 31, 2015.
Metwally H. et al. "Mechanism of Protein Supercharging by Sulfolane and m-Nitrobenzyl Alcohol: Molecular Dynamics Simulations of the Electrospray Process." Anal Chem. May 17, 2016;88(10):5345-54. doi: 10.1021/acs.analchem.6b00650. Epub Apr. 27, 2016.
Ogorzalek Loo RR. et al. "What protein charging (and supercharging) reveal about the mechanism of electrospray ionization." J Am Soc Mass Spectrom. Oct. 2014;25(10):1675-93. doi: 10.1007/s13361-014-0965-1. Epub Aug. 19, 2014.
Richardson, S. "Environmental mass spectrometry." Anal. Chem. 2000, 72, 4477-4496.

(Continued)

*Primary Examiner* — Paul S Hyun
(74) *Attorney, Agent, or Firm* — Womble Bond Dickinson (US) LLP; Deborah M. Vernon; Benedict L. Hanrahan

(57) ABSTRACT

The present disclosure relates devices and methods for analyzing intact antibodies, antibody subunits, antibody drug conjugate subunits, antibody drug conjugates, and intact proteins in a biological mixture.

17 Claims, 17 Drawing Sheets

(56) References Cited

OTHER PUBLICATIONS

Sack C. et al. "Collaborative validation of the QuEChERS procedure for the determination of pesticides in food by LC-MS/MS." J Agric Food Chem. Jun. 22, 2011;59(12):6383-411. doi: 10.1021/jf201618q. Epub May 27, 2011.

Sharon M. et al. "The role of mass spectrometry in structure elucidation of dynamic protein complexes." Annu Rev Biochem. 2007;76:167-93.

Staples GO. et al. "Improved hydrophilic interaction chromatography LC/MS of heparinoids using a chip with postcolumn makeup flow." Anal Chem. Jan. 15, 2010;82(2):516-22. doi: 10.1021/ac901706f.

Stephenson JL Jr. et al. "Charge manipulation for improved mass determination of high-mass species and mixture components by electrospray mass spectrometry." J Mass Spectrom. Jul. 1998;33(7):664-72.

Tang Liang et al. "Dependence of ion intensity in electrospray mass spectrometry on the concentration of the analytes in the electrosprayed solution" Anal. Chem., 1993, 65 (24), pp. 3654-3668, DOI: 10.1021/ac00072a020 Publication Date: Dec. 1993.

Van den Heuvel RH et al. "Native protein mass spectrometry: from intact oligomers to functional machineries." Curr Opin Chem Biol. Oct. 2004;8(5):519-26.

Zhou H. et al. "Advancements in top-down proteomics." Anal Chem. Jan. 17, 2012;84(2):720-34. doi: 10.1021/ac202882y. Epub Nov. 15, 2011.

Chambers et al. "Development of a fast method for direct analysis of intact synthetic insulins in human plasma: the large peptide challenge." Bioanalysis. 5.1(2013):65-81.

Chambers et al. "High sensitivity LC-MS/MS method for direct quantification of human parathyrois 1-34 (teriparatide) in human plasma." J. Chromatography B. 938(2013):96-104.

Chambers et al. "Multidimensional LC-MS/MS Enables Simultaneous Quantification of Intact Human Insulin and Five Recombinant Analogs in Human Plasma." Anal. Chem. 86.1(2013):694-702.

Chambers et al. "Practical applications of integrated microfluidics for peptide quantification." Bioanalysis. 7.7(2015):857-867.

\* cited by examiner

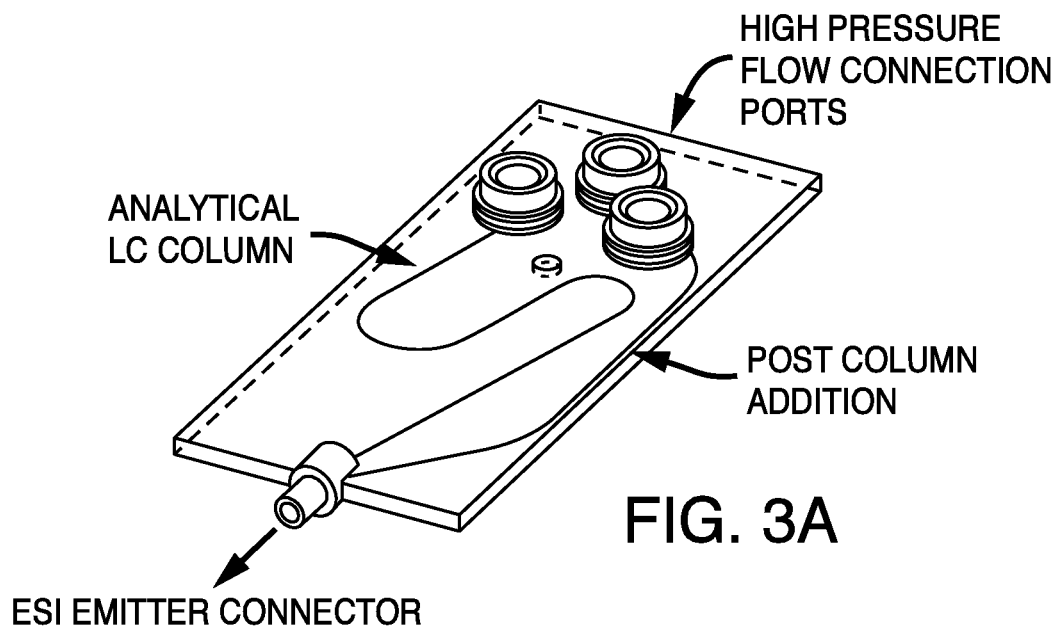
FIG. 3A
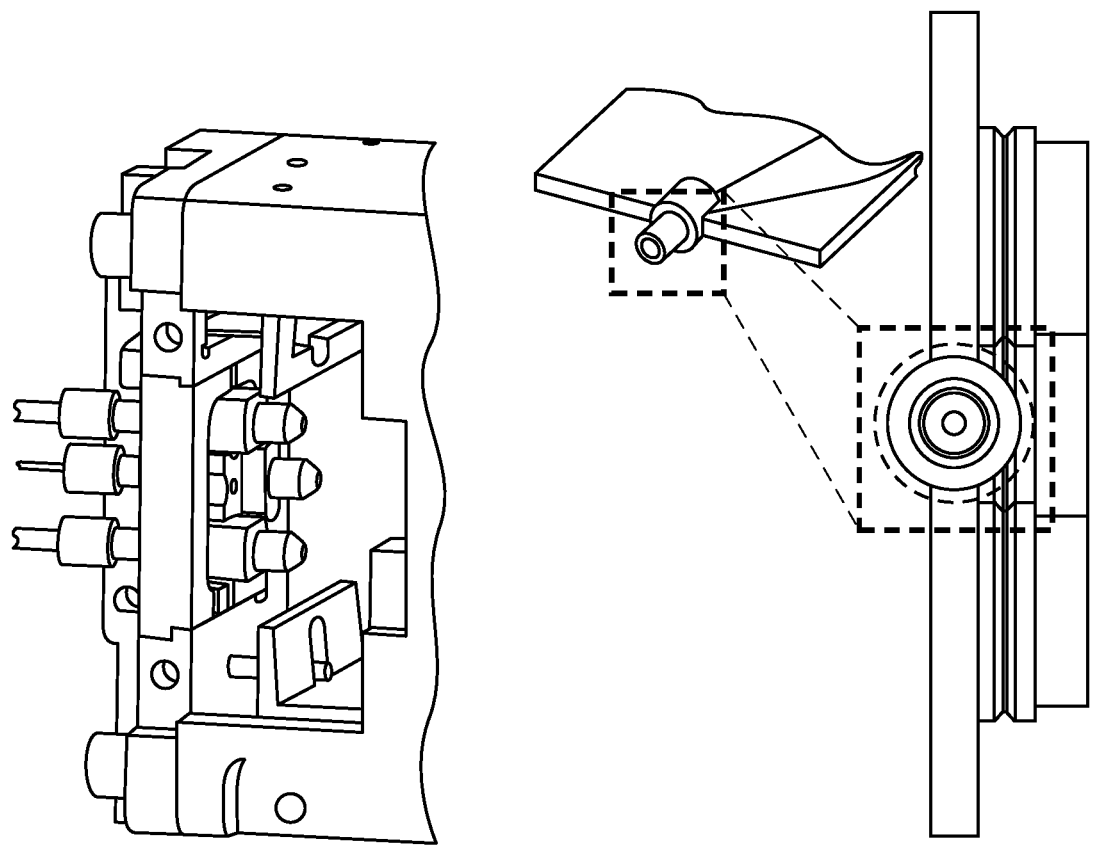
FIG. 3B
FIG. 3C

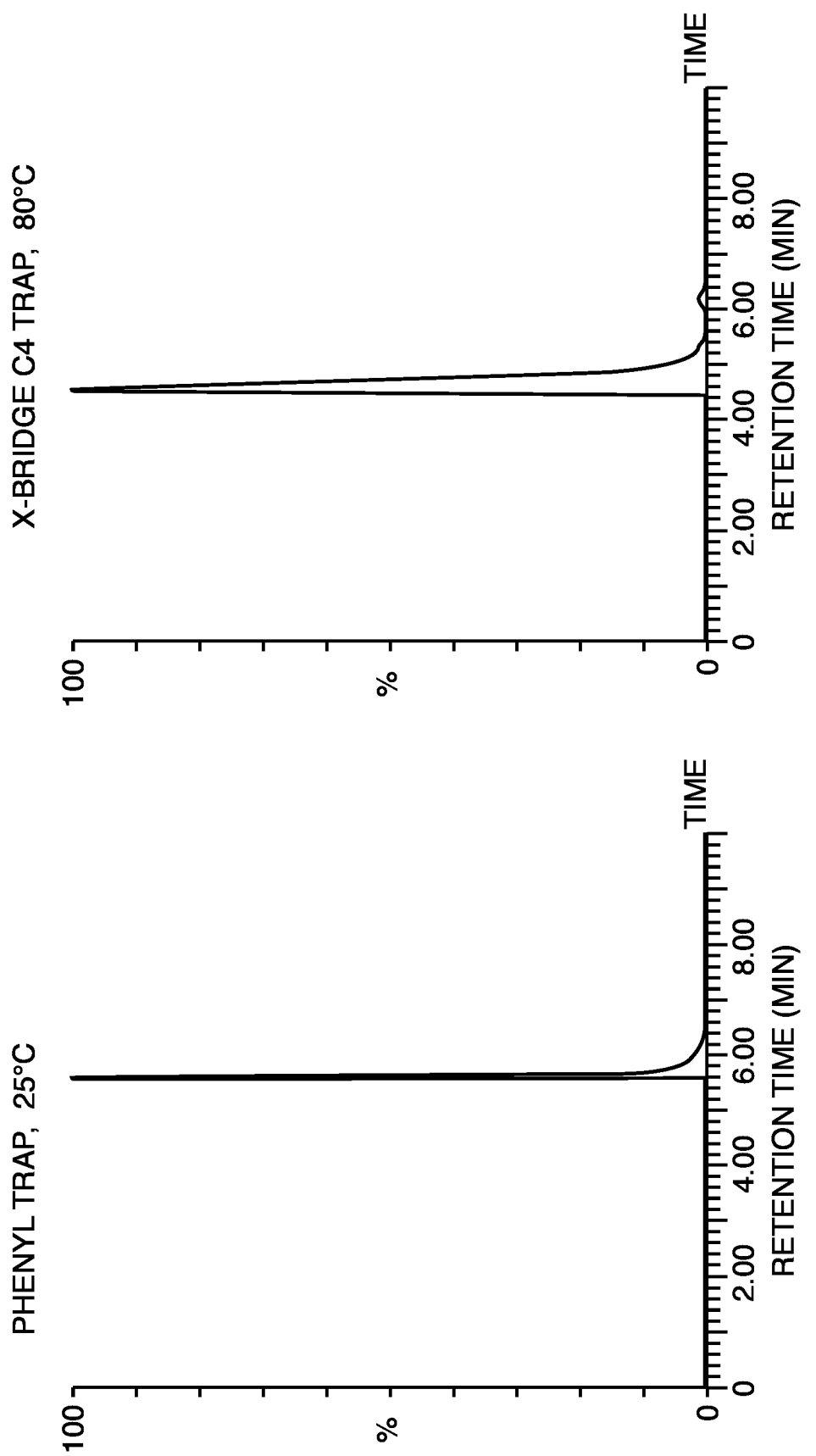

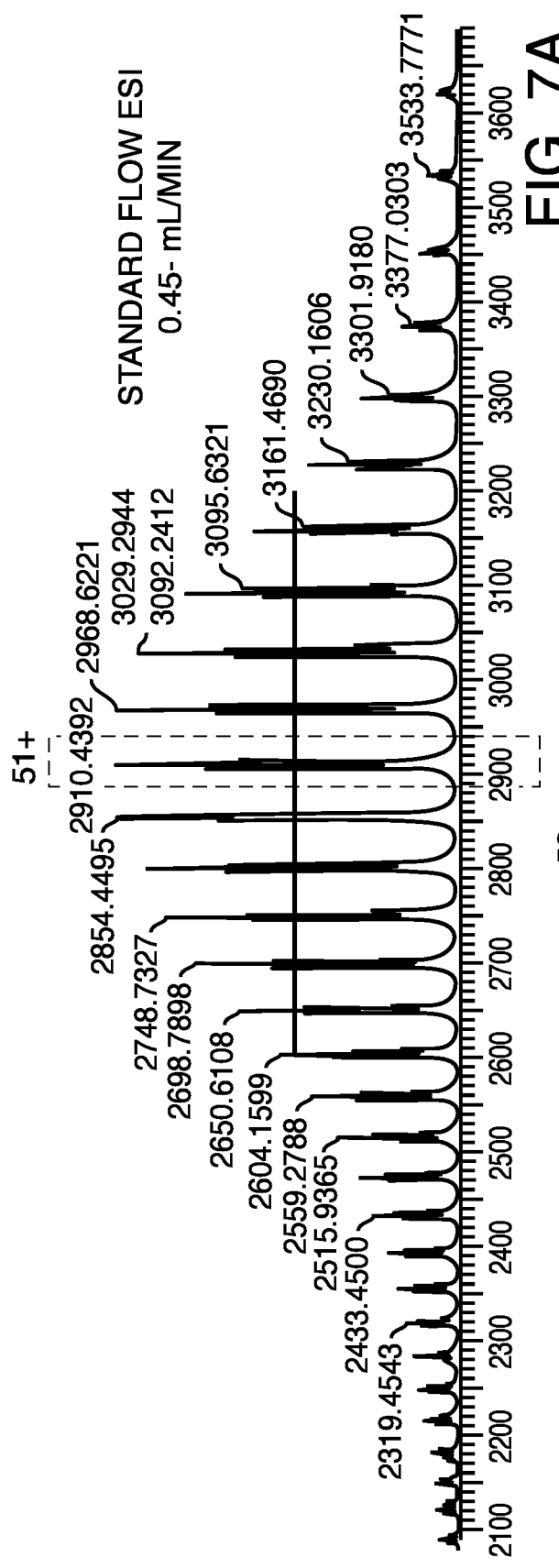
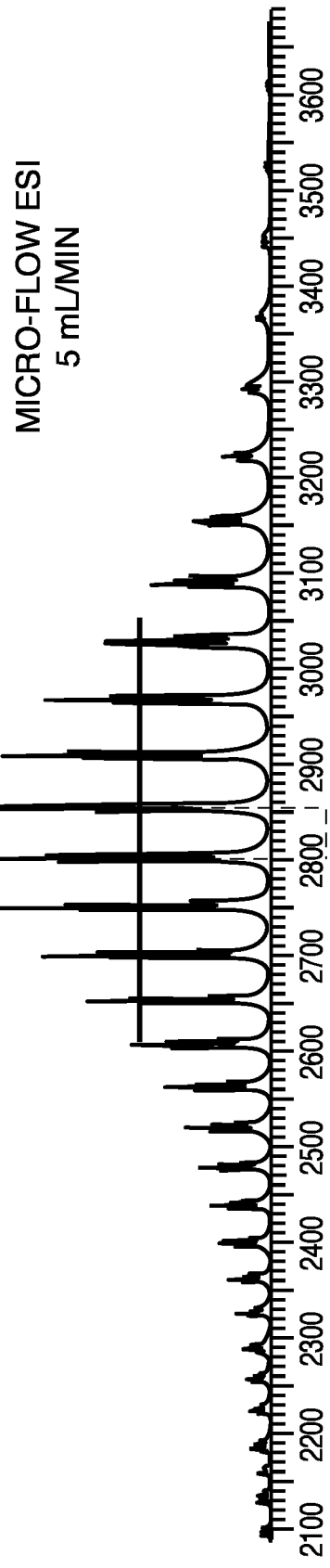
FIG. 7A
FIG. 7B

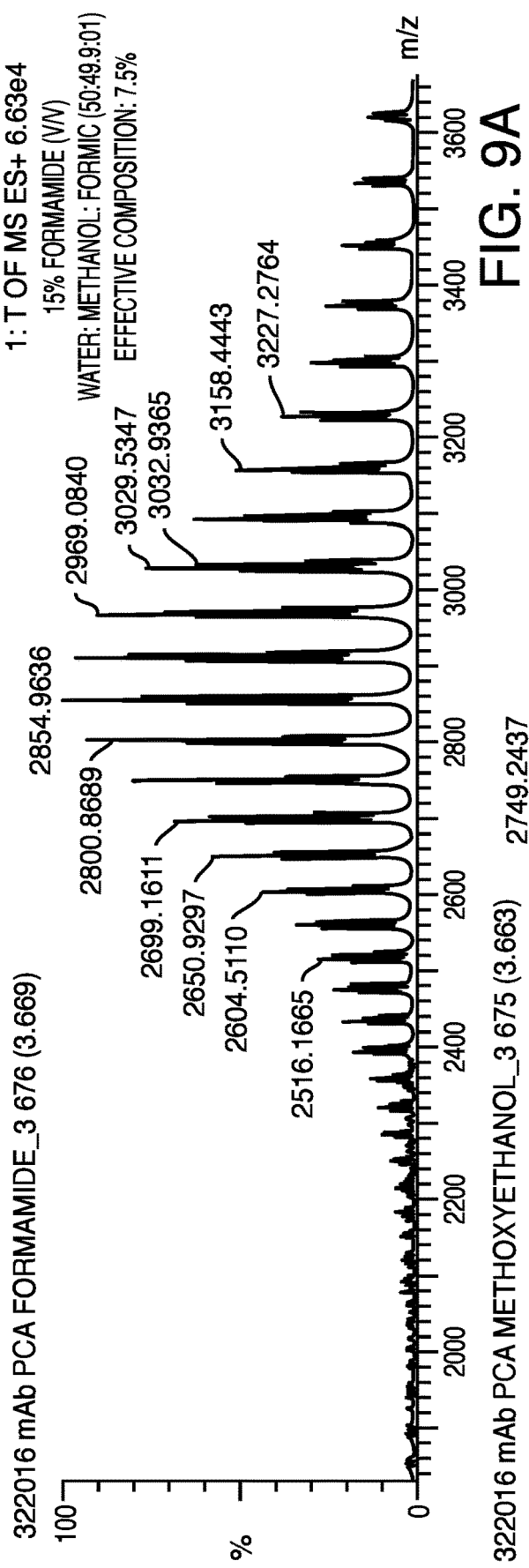
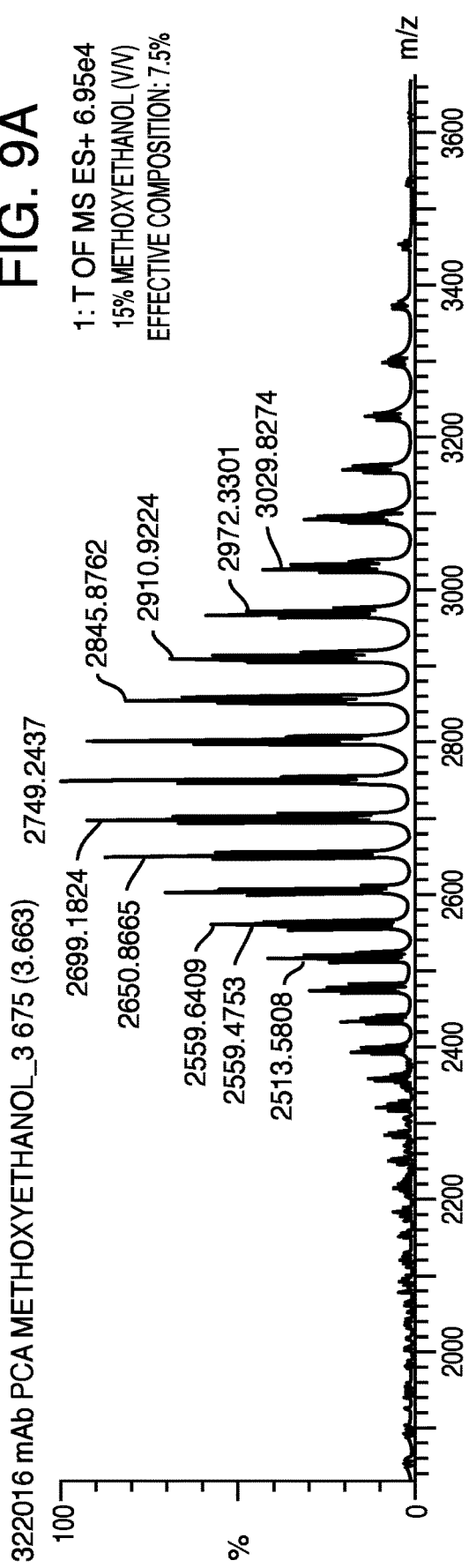
FIG. 9A
FIG. 9B

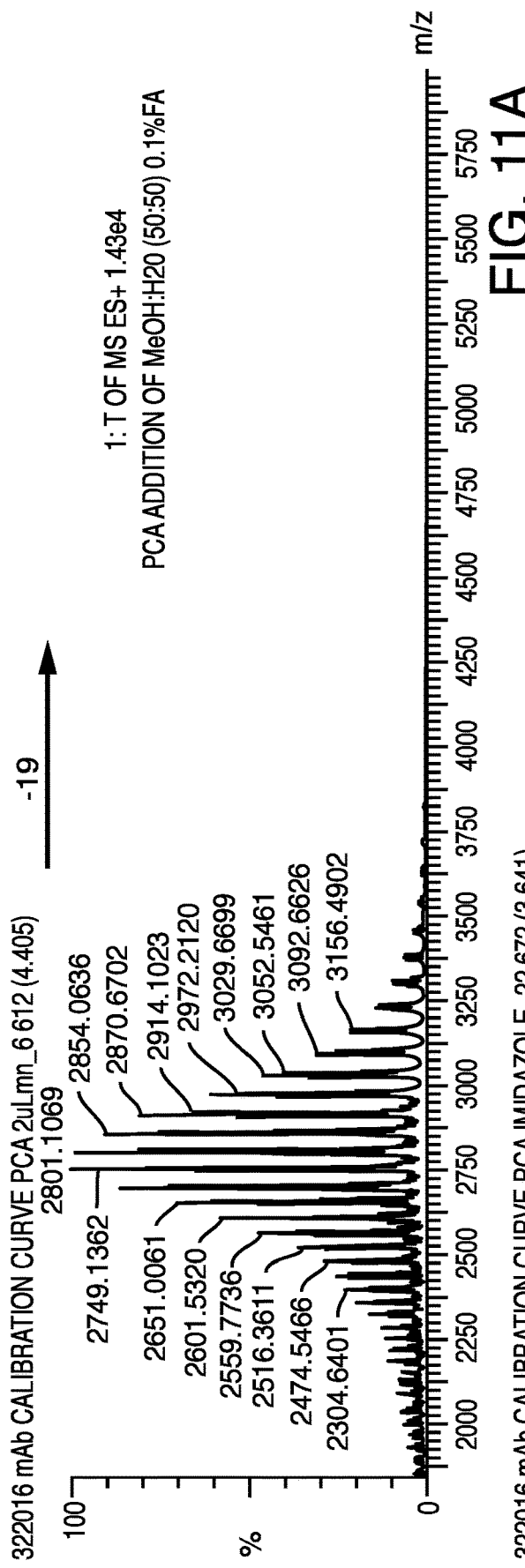
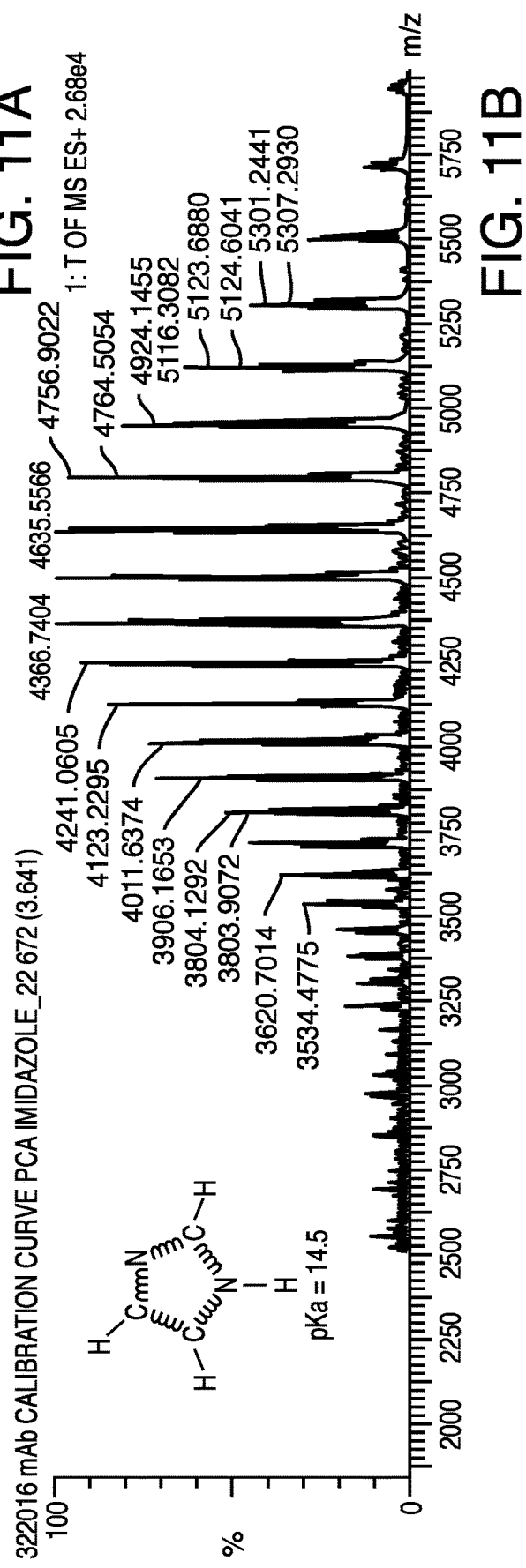
FIG. 11A
FIG. 11B

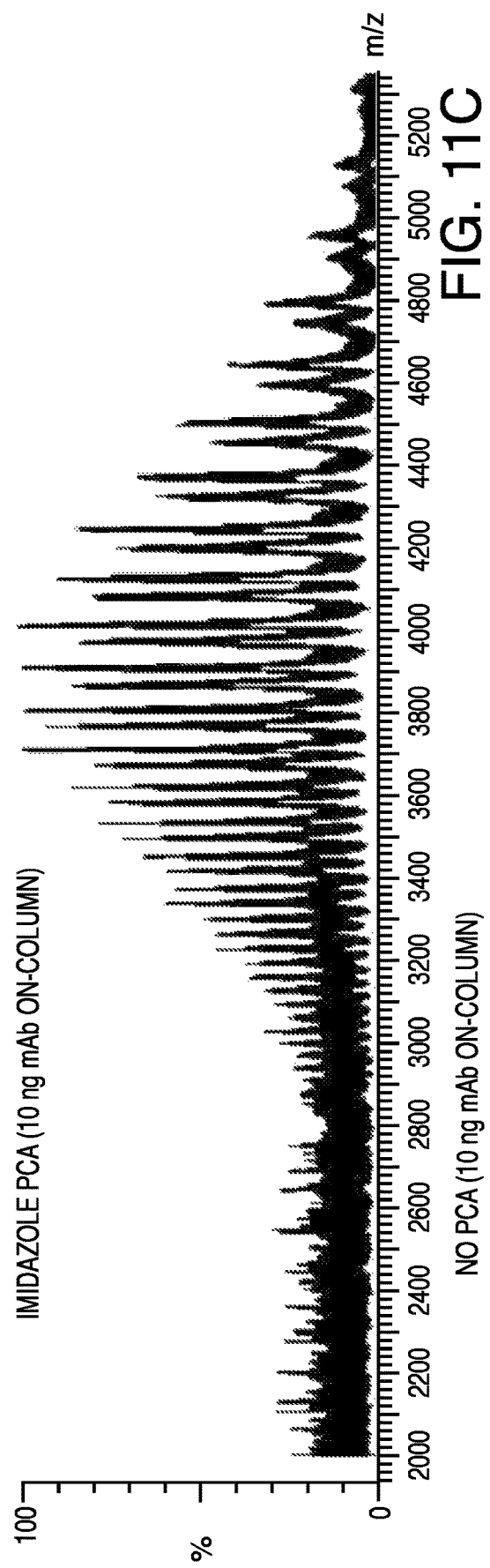
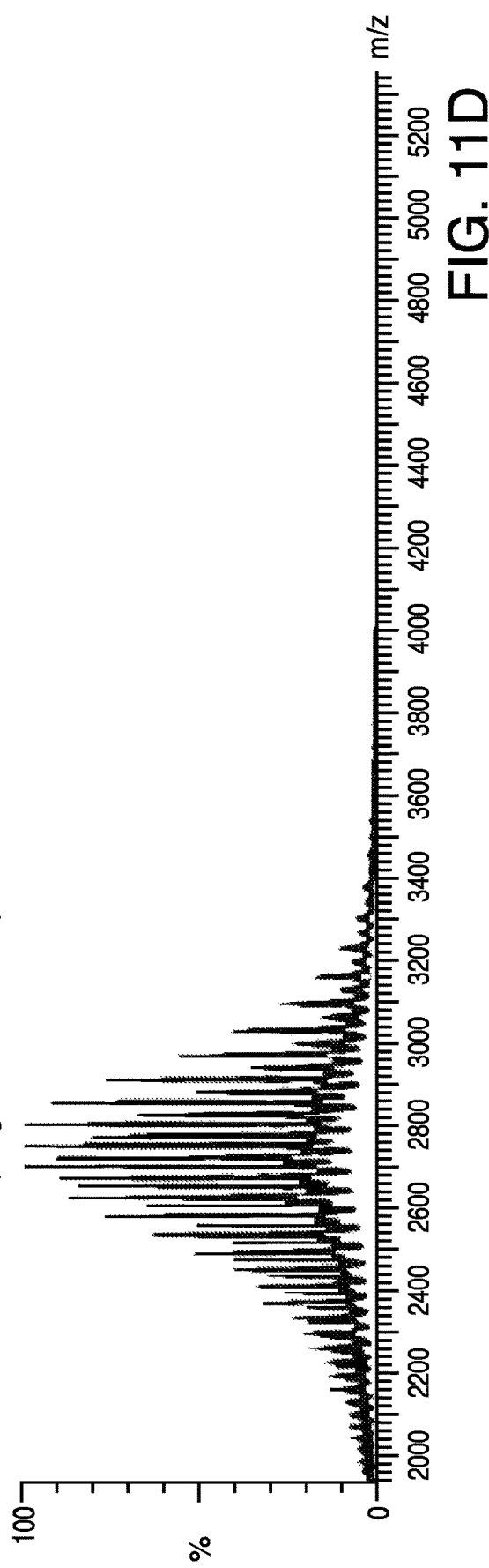
FIG. 11C
FIG. 11D

DEVICES AND METHODS FOR ANALYZING INTACT PROTEINS, ANTIBODIES, ANTIBODY SUBUNITS, AND ANTIBODY DRUG CONJUGATES

CROSS REFERENCE TO RELATED APPLICATIONS

This application claims benefit of and priority to U.S. Provisional Application No. 62/464,682 entitled "Devices and Methods for Analyzing Intact Proteins, Antibodies, Antibody Subunits, and Antibody Drug Conjugates," filed Feb. 28, 2017, the contents of which are incorporated herein by reference in its entirety.

FIELD OF THE INVENTION

The present disclosure relates devices and methods for analyzing intact antibodies, bispecific antibodies, antibody subunits, antibody drug conjugate subunits, antibody drug conjugates, and intact proteins in a biological mixture.

BACKGROUND

One of the biggest barriers associated with intact antibody analysis is the relative ionization efficiency using electrospray ionization (ESI) mass spectrometry. Well ionizing peptides and small molecules can easily be measured down to 1 pg/mL (~1 pM) using current technologies, such as liquid chromatography coupled with mass spectrometry (LC-MS). In comparison, the current technologies can measure deglycosylated antibodies with concentrations that only extend down to 0.1 µg/mL (~60 nM) in a neat solution. This approximate three order of magnitude difference in sensitivity is mainly due to the challenges of ionizing intact proteins via electrospray, which is significantly more challenged due to the molecular weight differential between intact antibodies and small molecules. The molecular weight of a protein also has a significant impact on the width of the charge state distributions (CSDs). As molecular weight increases, so does the width of the CSD, which results in a reduction of the signal to noise (S:N) by splitting ion current over a larger number of ions (Compton, P. D.; Zamdborg, L.; Thomas, P. M.; Kelleher, N. L. Anal. Chem. 2011, 83, 6868-6874). Accordingly, developing technologies that enable the narrowing of the CSD and increasing the charge state will further assist in improving sensitivity for the analysis of intact proteins.

SUMMARY OF THE INVENTION

The present disclosure relates devices and methods for analyzing intact antibodies, antibody subunits, antibody drug conjugate subunits, antibody drug conjugates, and intact proteins in a biological mixture, which provide significantly improved sensitivity, linearity, and resolution as compared to conventional high flow analytical LC-MS.

Accordingly, provided herein are methods for analyzing the components of a biological mixture. One embodiment of the method comprises at least three steps. One step involves providing a sample comprising one or more of intact antibodies or fragments thereof, antibody drug conjugates or subunits thereof, or intact proteins. Another step involves exposing the sample to a first dimension comprising a trap. Another step involves exposing the sample to a second dimension comprising a stationary phase. Then the components of the sample are separated. Subsequently, a mass to charge ratio of each of the components in the sample is established.

Optionally, the method may also include another step wherein some separation occurs on the trap such that when the sample is loaded onto the trap, small ions are removed the sample ("desalting"). This optional step occurs on the trap when the sample is eluted from the trap to the second dimension such that further separation occurs. The chemistry of the trap and the chemistry of the second dimension must be matched appropriately to provide optimal peak shape.

Another embodiment of the method comprises at least four steps. One step involves providing a sample comprising one or more of intact antibodies or fragments thereof, antibody drug conjugates or subunits thereof, or intact proteins. Another step involves exposing the sample to a first dimension separation. Another step involves exposing the sample to a second dimension separation. Another step involves adding a supercharging or a decharging reagent to the sample using a post column addition (PCA) microflow device. Then the components of the sample are separated. Subsequently, a mass to charge ratio of each of the components in the sample is established. In some embodiments, the microflow device comprises microfluidic based system. Alternatively, the microflow device can comprise a capillary based system.

Also provided herein are devices comprising at least four components. One component is a first dimension separator, such as, for example, a trap. Another component is a second dimension separator, such as, for example a stationary phase. Another component is a post column addition (PCA) microflow device. Another component is a mass spectrometer. In some embodiments, the device further comprises an ultraviolet/visible (UV/Vis) spectrometer. In other embodiments, the mass spectrometer is a quadrupole time-of-flight (QToF) mass spectrometer. In particular embodiments, the microflow device comprises microfluidic based system. Alternatively, the microflow device can comprise a capillary based system.

The methods and devices provided herein enable isolation, purification, analysis, and detection of intact antibodies, antibody subunits, antibody drug conjugate subunits, antibody drug conjugates, and intact proteins in a biological mixture using a two dimensional microscale separation.

The technology relates to a method for analyzing the components of a biological mixture. The method includes (i) providing a sample comprising one or more of intact antibodies or fragments thereof, antibody drug conjugates or subunits thereof, or intact proteins; (ii) exposing the sample to a first dimension comprising a trap; (iii) exposing the sample to a second dimension comprising a stationary phase; (iv) separating the components of the sample; and (v) establishing a mass to charge ratio of each of the components in the sample.

The method can also include the step of detecting each of the components in the sample. Ultraviolet (UV) and/or visible light spectroscopy can be used to detect each of the components in the sample. The detecting step can be performed prior to exposing the sample to the second dimension. The detecting step can be performed between exposing the sample to the first dimension and the second dimension.

The method can also include adding a supercharging reagent to the sample. The supercharging reagent can be selected from the group consisting of formamide, methoxyethanol, glycerol, and m-nitrobenzyl alcohol (m-NBA). The supercharging reagent can be glycerol. The supercharging reagent can be added to the sample after exposing the sample to the second dimension. The supercharging reagent can be added to the sample between exposing the sample to the second dimension and establishing a mass to charge ratio of each of the components in the sample. The supercharging reagent can be added to the sample using a microflow device.

The method can also include adding a decharging reagent to the sample. The decharging reagent can be imidazole. The decharging reagent can be added to the sample after exposing the sample to the second dimension. The decharging reagent can be added to the sample between exposing the sample to the second dimension and establishing a mass to charge ratio of each of the components in the sample. The decharging reagent can be added to the sample using a microflow device.

The microflow device can be a post column addition (PCA) microflow device. The microflow device can include a microfluidic based system. The microflow device can include a capillary based system.

The technology relates to a method for analyzing the components of a biological mixture. The method includes: (i) providing a sample comprising one or more of intact antibodies or fragments thereof, antibody drug conjugates or subunits thereof, or intact proteins; (ii) exposing the sample to a first dimension separation; (iii) exposing the sample to a second dimension separation; (iv) adding a supercharging or a decharging reagent to the sample using a post column addition (PCA) microflow device; (v) separating the components of the sample; and (vi) establishing a mass to charge ratio of each of the components in the sample.

The first dimension separation can include trapping a portion of the sample on a first stationary phase. The second dimension separation can include exposing the sample to a second stationary phase.

The method can also include the step of detecting each of the components in the sample.

Ultraviolet (UV) and/or visible light spectroscopy can be used to detect each the components in the sample.

The detecting step can be performed prior to exposing the sample to the second dimension. The detecting step can be performed between exposing the sample the first dimension and the second dimension.

The supercharging reagent can be selected from the group consisting of formamide, methoxyethanol, glycerol, and m-nitrobenzyl alcohol (m-NBA). The supercharging reagent can be glycerol.

The decharging reagent can be imidazole.

The microflow device can include a microfluidic based system. The microflow device can include a capillary based system.

The sample can be a biological sample. The biological sample can be derived from a subject. The subject can be a human subject. The biological sample can be selected from the group consisting of blood or derived from blood, tissue, urine, saliva, lymph, and biopsy. The biological sample can be blood or derived from blood. The biological sample can be plasma or serum.

The technology relates to a device that includes (i) a first dimension separator comprising a trap; a second dimension separator comprising a stationary phase; a post column addition (PCA) microflow device; and a mass spectrometer.

The device can include an ultraviolet/visible (UV/Vis) spectrometer.

The mass spectrometer can be a quadrupole time-of-flight (QToF) mass spectrometer.

The microflow device can include a microfluidic based system. The microflow device can include a capillary based system.

The above embodiments of the methods and devices described herein possess one or more advantages. For example, certain embodiments provide significantly improved sensitivity, linearity, and resolution as compared to conventional high flow analytical LC-MS. In some embodiments, one or more advantages is achieved by incorporation of two distinct chromatographic dimensions, providing the capability of tuning selectively in each dimension and thereby allowing for control of refocusing functionality. In certain embodiments, one or more advantages is achieved or improved by pairing trapping chemistry with analytical chemistry to optimize refocusing. In certain embodiment, one or more advantages is achieved or improved by microscale integration of UV detection between the first and second dimension separation, which enables refocusing of analyte that has been broadened by UV detector and tubings prior to ESI spray. In some embodiments, one or more advantages is achieved or enhanced by the addition of one or more supercharging and/or decharging reagents that retain glycoform resolution.

BRIEF DESCRIPTION OF THE DRAWINGS

FIG. 3 shows A: a microfluidic layout for the integrated microfluidic device; B: a clamping design that connects the outside fluidics to the microfluidic device shown in A; and C: an end on view of connection mechanism for emitter onto the end of the microfluidic device.

In FIG. 5A, the trap is packed, while the microfluidic device is not packed (open tubular) and FIG. 5C shows the corresponding chromatogram. In FIG. 5B, both trap and microfluidic LC are packed in this configuration and FIG. 5D shows the corresponding chromatogram. Separation is of IgG under neat conditions.

FIG. 6 A: illustrates the peak shape between the phenyl and X-bridge C4 trap paired with a BEH-C4 analytical microfluidic device. FIGS. 6B and 6C illustrate the dependency on peak width versus temperature for both the X-bridge C4 trap (6B) and the phenyl trap (6C).

FIGS. 9A-9D show supercharging screening for IgG shows optimized conditions.

DETAILED DESCRIPTION OF THE INVENTION

Figure 1:
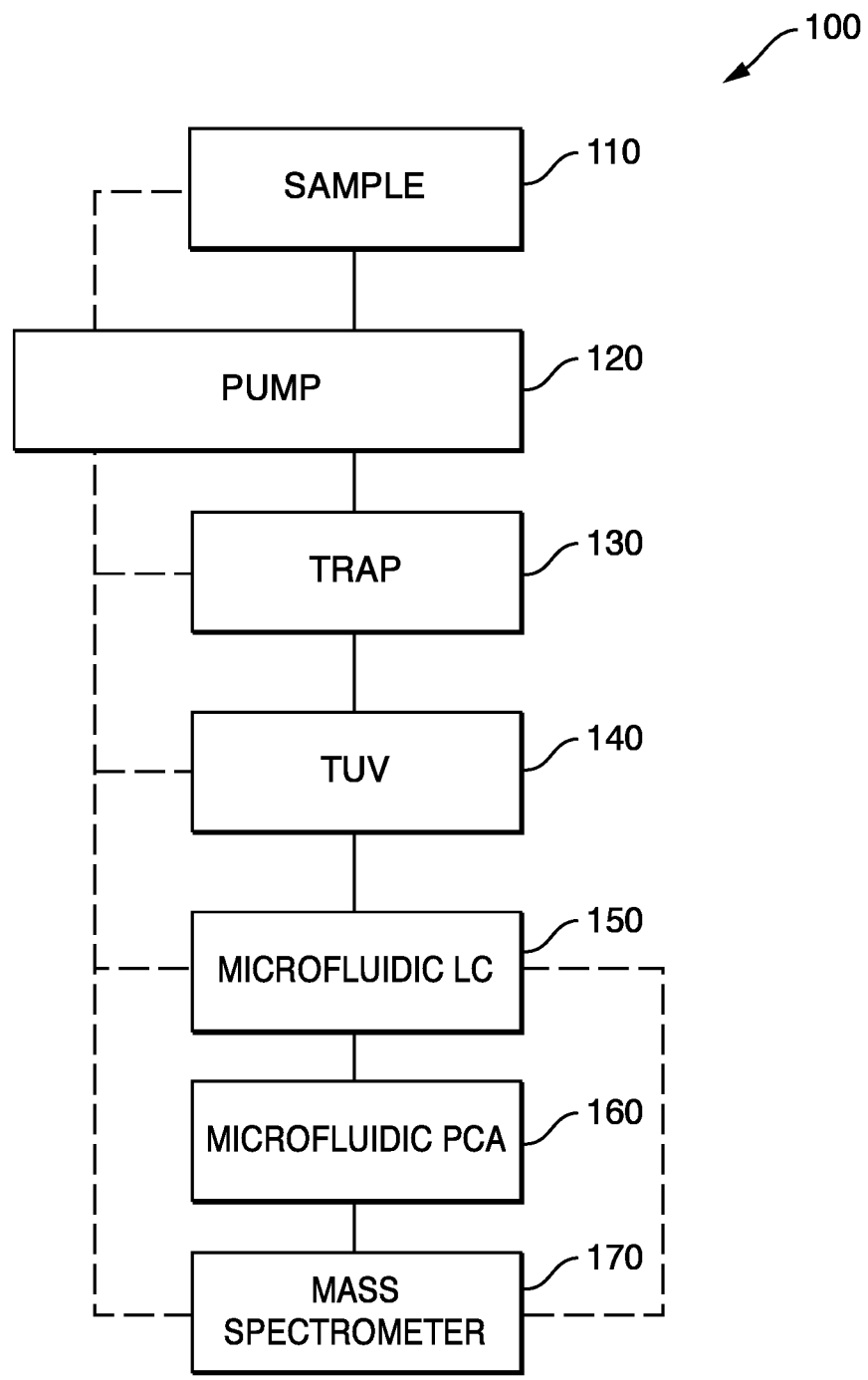
FIG. 1 shows an instrument flow diagram showing the components of one embodiment of the device disclosed herein.

Reference will now be made in detail to certain embodiments of the invention, examples of which are illustrated in the accompanying figures. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described.
Definitions Unless stated otherwise, the following terms and phrases as used herein are intended to have the following meanings:

As used herein "antibody drug conjugates: or "ADCs" are monoclonal antibodies (mAbs) attached to biologically active drugs by chemical linkers with labile bonds.

"Antibody" is used herein in the broadest sense and specifically covers monoclonal antibodies, polyclonal antibodies, multispecific antibodies (e.g., bispecific antibodies), and antibody fragments. Antibodies may be murine, human, humanized, chimeric, or derived from other species. An antibody is a protein generated by the immune system that is capable of recognizing and binding to a specific antigen. (Janeway, et al (2001) "Immunobiology", 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody.

Antibody also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "linker unit" refers to the direct or indirect linkage of the antibody to the drug. Attachment of a linker to a mAb can be accomplished in a variety of ways, such as through surface lysines, reductive-coupling to oxidized carbohydrates, and through cysteine residues liberated by reducing interchain disulfide linkages. A variety of ADC linkage systems are known in the art, including hydrazone-, disulfide- and peptide-based linkages.

The term "active pharmaceutical ingredient" or "API" refers to is the ingredient in a pharmaceutical drug that is biologically active. The terms "pharmaceutical drug," "drug," and "payload" are used interchangeably throughout, and refer to any substance having biological or detectable activity, for example, therapeutic agents, detectable labels, binding agents, etc., and prodrugs, which are metabolized to an active agent in vivo.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z").

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), ultra-high performance liquid chromatography (UHPLC), turbulent flow liquid chromatography (TFLC) (sometimes known as high turbulence liquid chromatography (HTLC) or high throughput liquid chromatography).

As used herein, the term "high performance liquid chromatography" or "HPLC" (also sometimes known as "high pressure liquid chromatography") refers to liquid chromatography in which the degree of separation is increased by forcing the mobile phase under pressure through a stationary phase, typically a densely packed column. As used herein, the term "ultra high performance liquid chromatography" or "UHPLC" (sometimes known as "ultra high pressure liquid chromatography") refers to HPLC that occurs at much higher pressures than traditional HPLC techniques.

The term "LC/MS" refers to a liquid chromatograph (LC) interfaced to a mass spectrometer.
Devices of the Invention The invention provides devices for isolating, purifying, analyzing, and/or detecting, intact antibodies, antibody subunits, antibody drug conjugate subunits, antibody drug conjugates, and intact proteins in a biological mixture using a two dimensional microscale separation. The methods and devices described herein provide significantly improved sensitivity, linearity, and resolution as compared to conventional high flow analytical LC-MS. In some embodiments, the LC-MS is a micro-flow LC-MS, which allow for greater sensitivity.

Accordingly, provided herein are devices comprising at least four components. One component is a first dimension separator comprising a trap. Another component is a second dimension separator comprising a stationary phase. Another component is a post column addition (PCA) microflow device. Another component is a mass spectrometer. In some embodiments, the device further comprises an ultraviolet/visible (UV/Vis) spectrometer. In other embodiments, the mass spectrometer is a quadrupole time-of-flight (QToF) mass spectrometer. In particular embodiments, the microflow device comprises microfluidic based system. Alternatively, the microflow device can comprise a capillary based system.

In one embodiment, the devices provided herein are designed to analyze antibodies, antibody drug conjugates, and antibody subunits using two dimensional LC coupled with microfluidic PCA and in-line coupled TUV-MS detection. The sample is collected in the sample manager and has a number of potential paths for analysis illustrated in FIG. 1. The integration and adaptability of this system 100 incorporates a sample manager 110, pump 120, trapping valve manager 130, fiber optic coupled TUV flow cell 140, microfluidic LC tile 150, post-column microfluidic 160, and mass spectrometer 170. As illustrated in FIG. 1, the sample can pass through each component in series along the flowpath illustrated by a straight line. Alternatively, the sample can take an alternative route. The dotted line in FIG. 1 represents alternative paths for the sample. It is possible to configure the instrument in a number of different configurations. An important factor is to minimize extra column volume. One system configuration in FIG. 1 addresses this factor by including a UV detector (TUV flow cell 140) after the first dimension separation (trap 130), but before the microfluidic LC tile 150 (second dimension separation). As a result, the sample is cleaned up prior to UV detection, but then refocused on the second dimension for analysis by ESI-MS. In some embodiments, following this process of refocusing and separation on a microfluidic device, post column additions of a supercharging or decharging reagent is added to the sample containing the antibody to add specific functionality.

Methods of the Invention

The invention also provides methods for isolating, purifying, analyzing, and/or detecting, intact antibodies, antibody subunits, antibody drug conjugate subunits, antibody drug conjugates, and intact proteins in a biological mixture using a two dimensional microscale separation. The methods and devices described herein provide significantly improved sensitivity, linearity, and resolution as compared to conventional high flow analytical LC-MS.

Microscale separation refers to separation systems that are miniaturized such that they significantly improve heat and mass transfer, expanding design choices and analysis capabilities. Microfabricated devices also benefit in terms of their readiness for system integration. This separation technique features reduced reagent consumption, improved performance and multifunctionality by utilizing interconnected network of channels, and inexpensive mass production. Microfluidic systems accommodate incorporation of various sample preparation steps and can be connected to such sophisticated detection systems, such as MS.

Accordingly, provided herein are methods for analyzing the components of a biological mixture. One embodiment of the method comprises at least three steps. One step involves providing a sample comprising one or more of intact antibodies or fragments thereof, antibody drug conjugates or subunits thereof, or intact proteins. Another step involves exposing the sample to a first dimension comprising a trap. Another step involves exposing the sample to a second dimension comprising a stationary phase. Then the components of the sample are separated. Subsequently, a mass to charge ratio of each of the components in the sample is established.

Another embodiment of the method comprises at least four steps. One step involves providing a sample comprising one or more of intact antibodies or fragments thereof, antibody drug conjugates or subunits thereof, or intact proteins. Another step involves exposing the sample to a first dimension separation. In some embodiments, the first dimension separation comprises trapping a portion of the sample on a first stationary phase. Another step involves exposing the sample to a second dimension separation. In some embodiments, the second dimension separation comprises exposing the sample to a second stationary phase. Another step involves adding a supercharging or a decharging reagent to the sample using a post column addition (PCA) microflow device. Then the components of the sample are separated. Subsequently, a mass to charge ratio of each of the components in the sample is established.

The methods disclosed herein can further comprise the step of detecting each of the components in the sample. In some embodiments, ultraviolet (UV) and/or visible light spectroscopy is used to detect each the components in the sample. In particular embodiments, the detecting step is performed prior to exposing the sample to the second dimension. In other embodiments, the detecting step is performed between exposing the sample the first dimension and the second dimension.

In some embodiments, the methods disclosed herein utilize a microflow device. In a particular embodiment, the microflow device comprises a microfluidic based system. Alternatively, the microflow device can comprise a capillary based system.

Supercharging

Supercharging offers a unique route to further improve ionization efficiency and sensitivity beyond the capabilities of micro and nano-flow ESI alone (Iavarone, A. T.; Jurchen, J. C.; Williams, E. R. Anal. Chem. 2001, 73, 1455-1460). A supercharging reagent can be added prior to the ESI tip (post column), whose physical properties include low volatility, weak Bronsted basicity, and capability of interacting with the analyte. A very weak Bronsted base has the effect of decreasing the population of carboxylate anions, while simultaneously increasing the protonation of primary amines located on the antibody (Ogorzalek Loo, R. R.; Lakshmanan, R.; Loo, J. A. J. Am. Soc. Mass Spectrom., 2014, 25, 1675-1693). This increase in protonation of the weak acids present on the protein will shift the CSD to lower m/z, yielding a supercharged structure without structural modification.

Alternative mechanisms have employed the relatively low volatility of supercharging agents. As the droplet evaporates mobile phase at a greater rate than the supercharging reagent the concentration of the supercharging reagent enriches significantly. This high concentration of supercharging reagent can serve as a charge trap by forming a supercharging reagent shell surrounding the antibody (Metwally, H.; McAllister, R. G.; Popa, V.; Konermann, L. Anal. Chem.

2016, 88, 5345-5354). The theoretical S:N gains using a supercharging reagent can be approximated with equation 1.

$$\text{Number of Charges} = 59(S:N) \quad \text{Eq 1:}$$

Eq. 1 may be considered a ratio between a supercharging experiment and a baseline non-supercharging experiment, Eq. 1 can be reworked into Eq. 2 and 3 which yield a relationship between the charge shift ($\Delta$Charge) and the S:N enhancement ($\Delta$S:N). However, the change in signal to noise assumes equivalent chemical noise backgrounds between supercharging experiments, which is an important experimental variable.

$$\frac{\text{Number of } Charges_1}{\text{Number of } Charges_2} = \frac{S:N_1}{S:N_2} \quad \text{Eq. 2}$$

$$\Delta\text{Charge} = \Delta S:N \quad \text{Eq. 3}$$

In some embodiments, the methods disclosed herein comprise adding a supercharging reagent to the sample. Exemplary supercharging reagents include, but are not limited to formamide, methoxyethanol, glycerol, and m-nitrobenzyl alcohol (m-NBA). In preferred embodiments, the supercharging reagent is glycerol.

Decharging

In addition to supercharging, pH modifications of a molecule that has acidic or basic functionalities can shift the charge state leading to higher mass-to-charge ratios, referred to as charge stripping or decharging (Stephenson, J. L.; McLuckey, S. A. J. Mass Spectrometry 1998, 33, 664-672). The implications of pH modification are dependent upon the ionization mode, and the analyte of interest. Post column addition of pH modifiers can enable the greatest flexibility by separating the chromatographic performance from the ESI spray efficiency. The significance of shifting the overall charge state distribution to lower charge state and higher m/z has implications to providing better charge state resolution. In cases of antibodies with multiple glycosylation sites, post translational modifications, and drug conjugates, the charge state spectra can be very complex. In many cases, deglycosylation is required, to further simplify proteins due to overlapping charge states. Shifting these high mass ions to lower charge state affords improved charge state spacing resolution and deconvolution outcomes. There are also limitations with this approach in the form of sensitivity decreases due to the lower charge of the antibody. However, some of the losses associated with decreased signal are made up for by reduction of the chemical noise that is present in the LC-MS separation de facto.

Accordingly, in some embodiments, the methods disclosed herein comprise adding a decharging reagent to the sample. Exemplary decharging reagents include, but are not limited to Perfluoro-1, 3 dimethylcyclohexane (PDCH). In preferred embodiments, the decharging reagent is imidazole.

Detection Techniques

Methods of the present technology include one or more detection or detecting steps. For example, some embodiments utilize mass spectrometry for detection of the antibody-drug conjugate compound and the unconjugated drug compound in the sample. In some embodiments, mass spectrometry is used to establish a mass to charge ratio of each of the antibody-drug conjugate compound and the unconjugated drug compound in the sample.

In certain other embodiments, optical spectroscopy is used as the preferred detection technique. In a particular embodiment, ultraviolet (UV) and/or visible spectroscopy or fluorescence spectroscopy is used.

Mass Spectrometry

A variety of mass spectrometry systems capable of high mass accuracy, high sensitivity, and high resolution are known in the art and can be employed in the methods and devices of the invention. The mass analyzers of such mass spectrometers include, but are not limited to, quadrupole (Q), time of flight (TOF), ion trap, magnetic sector or FT-ICR or combinations thereof. The ion source of the mass spectrometer should yield mainly sample molecular ions, or pseudo-molecular ions, and certain characterizable fragment ions. Examples of such ion sources include atmospheric pressure ionization sources, e.g. electrospray ionization (ESI) and Matrix Assisted Laser Desorption Ionization (MALDI). ESI and MALDI are the two most commonly employed methods to ionize proteins for mass spectrometric analysis. ESI and APC1 are the most commonly used ion source techniques for LC/MS (Lee, M. "LC/MS Applications in Drug Development" (2002) J. Wiley & Sons, New York).

Surface Enhanced Laser Desorption Ionization (SELDI) is an example of a surface-based ionization technique that allows for high-throughput mass spectrometry (U.S. Pat. No. 6,020,208). Typically, SELDI is used to analyze complex mixtures of proteins and other biomolecules. SELDI employs a chemically reactive surface such as a "protein chip" to interact with analytes, e.g., proteins, in solution. Such surfaces selectively interact with analytes and immobilize them thereon. Thus, the analytes of the invention can be partially purified on the chip and then quickly analyzed in the mass spectrometer. By providing different reactive moieties at different sites on a substrate surface, throughput may be increased.

Commercially available mass spectrometers can sample and record the whole mass spectrum simultaneously and with a frequency that allows enough spectra to be acquired for a plurality of constituents in the mixture to ensure that the mass spectrometric signal intensity or peak area is quantitatively representative. This will also ensure that the elution times observed for all the masses would not be modified or distorted by the mass analyzer and it would help ensure that quantitative measurements are not compromised by the need to measure abundances of transient signals.

Optical Spectroscopy

A variety of optical spectroscopy systems capable of high accuracy, high sensitivity, and high resolution are known in the art and can be employed in the methods of the invention. Absorption spectroscopy refers to optical spectroscopic techniques that measure the absorption of radiation, as a function of frequency or wavelength, due to its interaction with a sample. The sample absorbs energy, i.e., photons, from the radiating field. The intensity of the absorption varies as a function of frequency, and this variation is the absorption spectrum. Absorption spectroscopy is performed across the electromagnetic spectrum.

Absorption spectroscopy is employed as an analytical chemistry tool to determine the presence of a particular substance in a sample and, in many cases, to quantify the amount of the substance present. Infrared and ultraviolet-visible spectroscopy are particularly common in analytical applications.

There are a wide range of experimental approaches for measuring absorption spectra. The most common arrangement is to direct a generated beam of radiation at a sample and detect the intensity of the radiation that passes through it. The transmitted energy can be used to calculate the absorption. The source, sample arrangement and detection technique vary significantly depending on the frequency range and the purpose of the experiment.

The most straightforward approach to absorption spectroscopy is to generate radiation with a source, measure a reference spectrum of that radiation with a detector and then re-measure the sample spectrum after placing the material of interest in between the source and detector. The two measured spectra can then be combined to determine the material's absorption spectrum. The sample spectrum alone is not sufficient to determine the absorption spectrum because it will be affected by the experimental conditions—the spectrum of the source, the absorption spectra of other materials in between the source and detector and the wavelength dependent characteristics of the detector. The reference spectrum will be affected in the same way, though, by these experimental conditions and therefore the combination yields the absorption spectrum of the material alone.

A wide variety of radiation sources can be employed in order to cover the electromagnetic spectrum. For spectroscopy, it is generally desirable for a source to cover a broad swath of wavelengths in order to measure a broad region of the absorption spectrum. Some sources inherently emit a broad spectrum. Examples of these include globars or other black body sources in the infrared, mercury lamps in the visible and ultraviolet and x-ray tubes. One recently developed, novel source of broad spectrum radiation is synchrotron radiation which covers all of these spectral regions. Other radiation sources generate a narrow spectrum but the emission wavelength can be tuned to cover a spectral range. Examples of these include klystrons in the microwave region and lasers across the infrared, visible and ultraviolet region (though not all lasers have tunable wavelengths).

The detector employed to measure the radiation power will also depend on the wavelength range of interest. Most detectors are sensitive to a fairly broad spectral range and the sensor selected will often depend more on the sensitivity and noise requirements of a given measurement. Examples of detectors common in spectroscopy include heterodyne receivers in the microwave, bolometers in the millimeter-wave and infrared, mercury cadmium telluride and other cooled semiconductor detectors in the infrared, and photodiodes and photomultiplier tubes in the visible and ultraviolet.

UV/Visible Spectroscopy

"Ultraviolet/visible spectroscopy" refers to absorption spectroscopy or reflectance spectroscopy in the ultraviolet (UV) and/or visible electromagnetic spectral region. Ultraviolet (UV) electromagnetic radiation can have a wavelength ranging from 100 nm (30 PHz) to 380 nm (750 THz), shorter than that of visible light but longer than X-rays. The visible light is a type of electromagnetic radiation that is visible to the human eye. Visible electromagnetic radiation can have a wavelength ranging from about 390 nm (430 THz) to about 700 nm (770 THz).

The instrument used in ultraviolet-visible spectroscopy is called a UV/Vis spectrophotometer. It measures the intensity of light passing through a sample (I), and compares it to the intensity of light before it passes through the sample ($I_o$). The ratio $I/I_o$ is called the transmittance, and is usually expressed as a percentage (% T). The absorbance, A, is based on the transmittance:

Fluorescence Spectroscopy

"Fluorescence spectroscopy" refers to a type of electromagnetic spectroscopy that analyzes fluorescence from a sample. It involves using a beam of light, usually ultraviolet light, that excites the electrons in molecules of certain compounds and causes them to emit light; typically, but not necessarily, visible light. A complementary technique is absorption spectroscopy. In the special case of single molecule fluorescence spectroscopy, intensity fluctuations from the emitted light are measured from either single fluorophores, or pairs of fluorophores.

Two general types of instruments exist: (1) filter fluorometers that use filters to isolate the incident light and fluorescent light; and (2) spectrofluorometers that use a diffraction grating monochromators to isolate the incident light and fluorescent light. Both types use the following scheme: the light from an excitation source passes through a filter or monochromator, and strikes the sample. A proportion of the incident light is absorbed by the sample, and some of the molecules in the sample fluoresce. The fluorescent light is emitted in all directions. Some of this fluorescent light passes through a second filter or monochromator and reaches a detector, which is usually placed at 90° to the incident light beam to minimize the risk of transmitted or reflected incident light reaching the detector.

Various light sources may be used as excitation sources, including lasers, LED, and lamps; xenon arcs and mercury-vapor lamps in particular. A laser only emits light of high irradiance at a very narrow wavelength interval, typically under 0.01 nm, which makes an excitation monochromator or filter unnecessary. A mercury vapor lamp is a line lamp, meaning it emits light near peak wavelengths. By contrast, a xenon arc has a continuous emission spectrum with nearly constant intensity in the range from 300-800 nm and a sufficient irradiance for measurements down to just above 200 nm.

Filters and/or monochromators may be used in fluorimeters. A monochromator transmits light of an adjustable wavelength with an adjustable tolerance. The most common type of monochromator utilizes a diffraction grating, that is, collimated light illuminates a grating and exits with a different angle depending on the wavelength. The monochromator can then be adjusted to select which wavelengths to transmit. For allowing anisotropy measurements the addition of two polarization filters are necessary: One after the excitation monochromator or filter, and one before the emission monochromator or filter.

As mentioned above, the fluorescence is most often measured at a 90° angle relative to the excitation light. This geometry is used instead of placing the sensor at the line of the excitation light at a 180° angle in order to avoid interference of the transmitted excitation light. No monochromator is perfect and it will transmit some stray light, that is, light with other wavelengths than the targeted. An ideal monochromator would only transmit light in the specified range and have a high wavelength-independent transmission. When measuring at a 90° angle, only the light scattered by the sample causes stray light. This results in a better signal-to-noise ratio, and lowers the detection limit by approximately a factor 10000, when compared to the 180° geometry. Furthermore, the fluorescence can also be measured from the front, which is often done for turbid or opaque samples.

The detector can either be single-channeled or multichanneled. The single-channeled detector can only detect the intensity of one wavelength at a time, while the multichanneled detects the intensity of all wavelengths simultaneously, making the emission monochromator or filter unnecessary. The different types of detectors have both advantages and disadvantages.

The most versatile fluorimeters with dual monochromators and a continuous excitation light source can record both an excitation spectrum and a fluorescence spectrum. When measuring fluorescence spectra, the wavelength of the excitation light is kept constant, preferably at a wavelength of high absorption, and the emission monochromator scans the spectrum. For measuring excitation spectra, the wavelength passing though the emission filter or monochromator is kept constant and the excitation monochromator is scanning. The excitation spectrum generally is identical to the absorption spectrum as the fluorescence intensity is proportional to the absorption.

Samples

In general, a sample used in the methods described herein is a composition known or suspected to contain intact antibodies, bispecific antibodies, antibody subunits, antibody drug conjugate subunits, antibody drug conjugates, and/or intact proteins. Samples can include a solid, liquid, gas, mixture, material (e.g., of intermediary consistency, such as a, extract, cell, tissue, organisms) or a combination thereof. In various embodiments, the sample is a biological sample. The term "biological sample" refers to a body fluid or a tissue of a living organism.

Biological samples can include any sample that is derived from the body of a subject. In this context, the subject can be an animal, for example a mammal, for example a human. Other exemplary subjects include a mouse, rat, guinea-pig, rabbit, cat, dog, goat, sheep, pig, cow, or horse. The individual can be a patient, for example, an individual suffering from a disease or being suspected of suffering from a disease. A biological sample can be a bodily fluid or tissue, for example taken for the purpose of a scientific or medical test, such as for studying or diagnosing a disease (e.g., by detecting and/or identifying a pathogen or the presence of a biomarker). Bodily samples can also include cells, for example, pathogens or cells of the individual bodily sample (e.g., tumor cells). Such bodily samples can be obtained by known methods including tissue biopsy (e.g., punch biopsy) and by taking blood, bronchial aspirate, sputum, urine, feces, or other body fluids. Exemplary bodily samples include humor, whole blood, plasma, serum, umbilical cord blood (in particular, blood obtained by percutaneous umbilical cord blood sampling (PUBS)), cerebrospinal fluid (CSF), saliva, amniotic fluid, breast milk, secretion, ichor, urine, feces, meconium, skin, nail, hair, umbilicus, gastric contents, placenta, bone marrow, peripheral blood lymphocytes (PBL), and solid organ tissue extract.

In one embodiment, the sample is a blood sample. In another embodiment, the sample is a blood-derived sample, such as plasma or serum.

In another embodiment, the sample is a cell sample. The cell sample can contain material obtained or derived from a subject. In other embodiments, the cell sample can contain cells from an in vitro or ex vivo cell culture. In other embodiments, the sample is a cell supernatant sample.

While it is recognized that the majority of samples used in the methods described herein will be bodily samples, samples derived from other sources known or suspected to contain antibodies may also be used in the disclosed methods. Such other samples include environmental samples, which may contain intact antibodies, antibody subunits, antibody drug conjugate subunits, antibody drug conjugates, and/or intact proteins due to, for example, the intentional or unintentional contamination of a given natural or manmade environment.

Environmental samples can include any sample that is derived from the environment, such as the natural environment (e.g., seas, soils, air, and flora) or the manmade environment (e.g., canals, tunnels, buildings). Such environmental samples can be used to discover, monitor, study, control, mitigate, and avoid environmental pollution. Exemplary environmental samples include water (e.g., drinking water, river water, surface water, ground water, potable water, sewage, effluent, wastewater, or leachate), soil, air, sediment, biota (e.g., soil biota), flora, fauna (e.g., fish), and earth mass (e.g., excavated material).

In some embodiments, the sample is a biological sample selected from whole blood, plasma, serum, umbilical cord blood, cerebrospinal fluid (CSF), saliva, amniotic fluid, breast milk, secretion, ichor, urine, feces, meconium, skin, nail, hair, umbilicus, gastric contents, placenta, bone marrow, peripheral blood lymphocytes (PBL), and solid organ tissue extract. In an exemplary embodiment, the sample is blood, plasma or serum.

INCORPORATION BY REFERENCE

The contents of all references, patents and published patent applications cited throughout this application, as well as the Figures, are hereby incorporated by reference in their entirety.

EXEMPLIFICATION

Having described the invention, the same will be more readily understood through reference to the following Example, which is provided by way of illustration, and are not intended to limit the invention in any way.

Example 1: Influence of Microflow, Supercharging, and Decharging on Whole Antibody Mass Spectrometry Using Microfluidic LC-MS An integrated microfluidic LC device coupled to a QTOF capable of improving sensitivity and linearity for intact protein analysis while also tuning the charge state distributions (CSD) of whole antibodies is demonstrated in this example. The mechanism for sensitivity improvement using microflow ESI was demonstrated by shifting of the CSD to higher charge state, and narrowing of the overall CSD. Both of these aspects served to improve ion current of the most abundant charge state of antibodies and lead to improvement in sensitivity over high flow ESI. In addition to improvements in sensitivity improvements in linear dynamic range for microflow ESI that results from a combination of lower limits of detection and narrower CSD were observed. Increasingly complex antibodies also were investigated for S:N comparisons relative to antibodies that were fully deglycosylated to demonstrate the deleterious effect of increasingly diverse CSD. In cases where the complexity of the antibody limited both sensitivity and spectral charge state resolution, supercharging and decharging mechanisms to further improve sensitivity and charge state spacing resolution were employed. An 89% increase in sensitivity using glycerol that was added post column, with retention of the glycoform resolution, was demonstrated. Additionally, a 51% increase in charge state resolution as imidazole was used to generate lower charge states for high-mass ions was demonstrated.

Methods and Materials:

Materials and Reagents:

Antibody IgG standards ($C_{6472}H_{9940}N_{1698}O_{2008}S_{52}$, Average MW: 145,329.7 Da, PN: 186006552) were purchased from Waters Cororation (Milford, Mass.). For deglycosylation of antibodies, peptide-N-glycosidase F (PNGase F) was purchased from New England Biolabs (Ipswitch, Mass.), and utilized standard deglycosylation procedure. PNGase F is an amidase which cleaves between the innermost GlcNac and asparagine residues from N-linked glycoproteins. Supercharging and decharging reagents, m-NBA, glycerol, and imidazole were purchased from Sigma Aldrich (St. Louis, Mo.). These compounds were prepared in 50:50 MeOH:H2O with 0.1% formic acid. LC-MS grade mobile phases A (0.1% formic acid in water) and mobile phase B (0.1% formic acid in acetonitrile) were purchased from Sigma-Aldrich (St. Louis, Mo.). Antibodies were diluted in 3% acetonitrile and 0.1% formic acid, which proved to be a stable solution over a 48 hr period. Max recovery vials (Waters, Milford, Mass. PN: 18600327c) were used to dilute and prepare antibody samples for injection.

Figure 2:
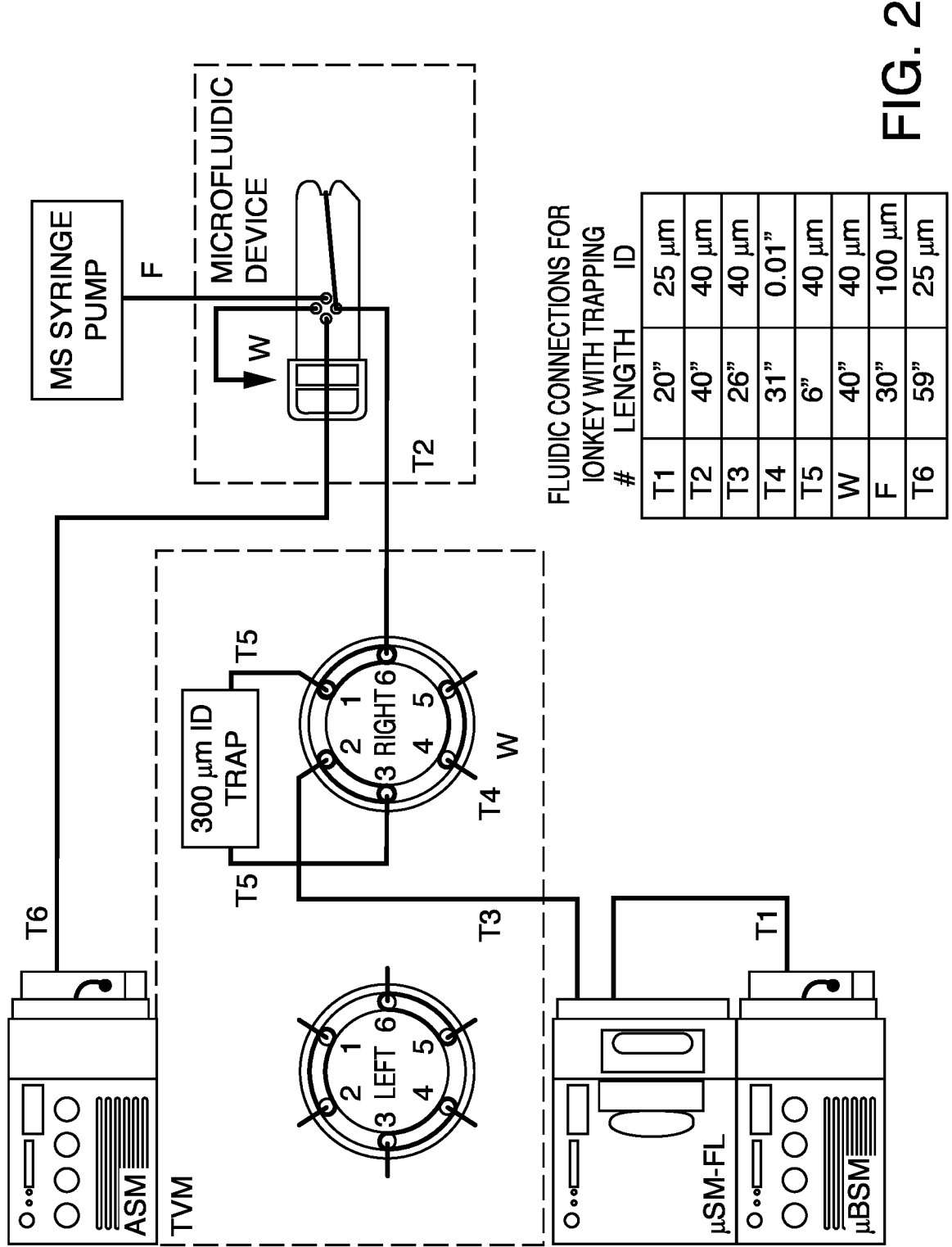
FIG. 2 is an illustration of the LC pump and trapping configuration for the 2D trap-wash-elute used in one embodiment of the methods disclosed herein.

First Dimension Trapping Columns:

Trapping columns were packed into 300 micron×5 cm stainless steel column bodies. The trap geometry was optimized for coupling to a 150 micron microfluidic LC device. The 300 micron ID was optimized based on protein load capabilities and refocusing capacity. Mechanical frits with 2.0 micron porosity were used to pack against and seal the inlet of the packed columns. Two different sorbents were used for these traps including: a) bridged-ethyl-hybrid particle conjugated to a C4 (5 micron particle size, 300 A porosity) and b) TSKgel Phenyl-5PW particle conjugated with a phenyl functionality (20 micron particle size, 1000 A porosity). Due to the large dimensions of the particle for these columns a relatively low packing pressure <5000 psi was required to efficiently pack these traps. The traps were operated under a thermostated condition. Elution from the trap was performed at the same flow rate as chromatographic elution through the microfluidic device (3 uL/min). Trap loading was performed at 0.1% B with a flow rate of 15 uL/min, performed for 1 min of loading time. Coupling of the trap to the microfluidic device was accomplished using a TVM. FIG. 2 illustrates the fluidic flow path for the trap coupled to the microfluidic LC device.

Microfluidic LC Devices:

Three different microfluidic devices were used for this study. These included: a) flow injection microfluidic device (unpacked, open tubular), b) LC separation microfluidic device, and c) LC separation with post column addition. The flow injection microfluidic device simply consists of an open manifold without any LC packings. This microfluidic device can be used for infusion experiments, or rapid method development for multi-dimensional analysis. The other two microfluidic devices either were integrated with and without post-column addition. FIG. 3A illustrates the complete high temperature cofired ceramic device integrated with high pressure flow connection ports, analytical LC column, post column addition, and a connector for the ESI emitter. FIG. 3B illustrates the mechanism that is used to connect the microfluidic device to the LC pump and autosampler. The high pressure flow connection ports are held in position, while the microfluidic device holder is depressed toward the high pressure connection ports to make a 10,000 psi seal. It is important to note here that all three ports are capable of withstanding the 10,000 psi pressure. PCA Emitter configuration is illustrated in FIG. 3C.

LC System:

The LC system comprised of an m-class binary solvent manager (BSM), a trap valve manager (TVM), an auxillary solvent manager (ASM) and a sample manager (SM) from Waters, Milford, Mass. The components and fluidic flow path is illustrated in FIG. 2. The LC gradient was linear starting at 3% mobile phase B (MPB) and increasing to 95% MPB in 3.5 min, followed by a 2.5 min hold at 95% and a 4 min requilibration. Strong needle wash was 50% acetonitrile, 25% iso-propanol, 25% $H_2O$ with 0.1% FA (V/V), weak needle wash was MPA.

Mass Spectrometer:

The MS system comprised of a Xevo G2-XS QTof with an ionKey source from Waters, Milford, Mass. For intact experiments the MS was scanned at a rate of 5 Hz, from 500 m/z to 4,000 m/z. Since the antibody has a charge state distribution that ranges from 2000 m/z to 3200 m/z this was acceptable to capture both the CSD of the protein and lock mass (Glu-fibrinopeptide B, 785.84265 m/z, +2 charge state). The RF collision cell voltage was optimized at 600 V, with a gain value of 10, while the quad profile was set to automatic mode. Data processing was performed using MassLynx and MaxEnt 1 deconvolution software.

Results and Discussion:

Trap and Microfluidic LC Chemistry Pairing

Figure 4:
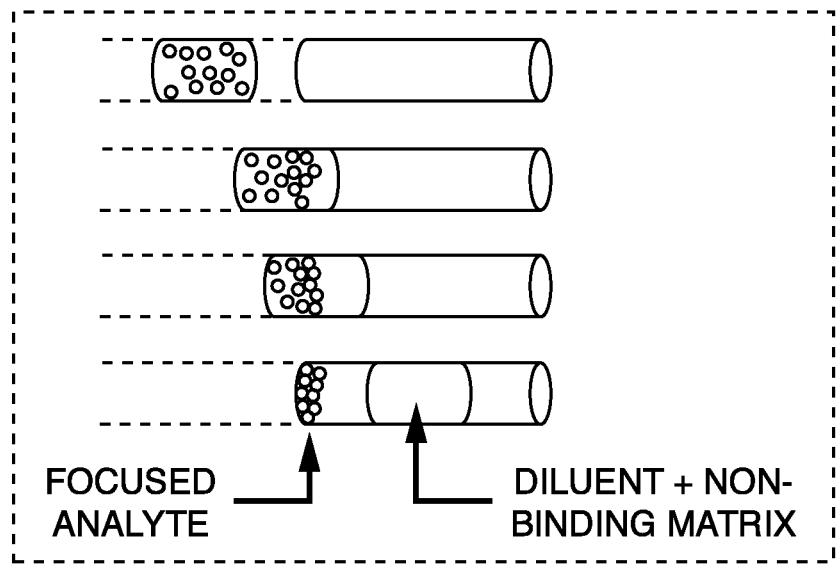
FIG. 4 shows a mechanism of loading the trap, focusing the analyte at the head of the trap and consequently removing diluent and non-binding matrix components (top); and a mechanism of moving the analyte from the first dimension trap, through transfer capillary, and refocusing the analyte on the microfluidic LC (bottom).
Figure 4:
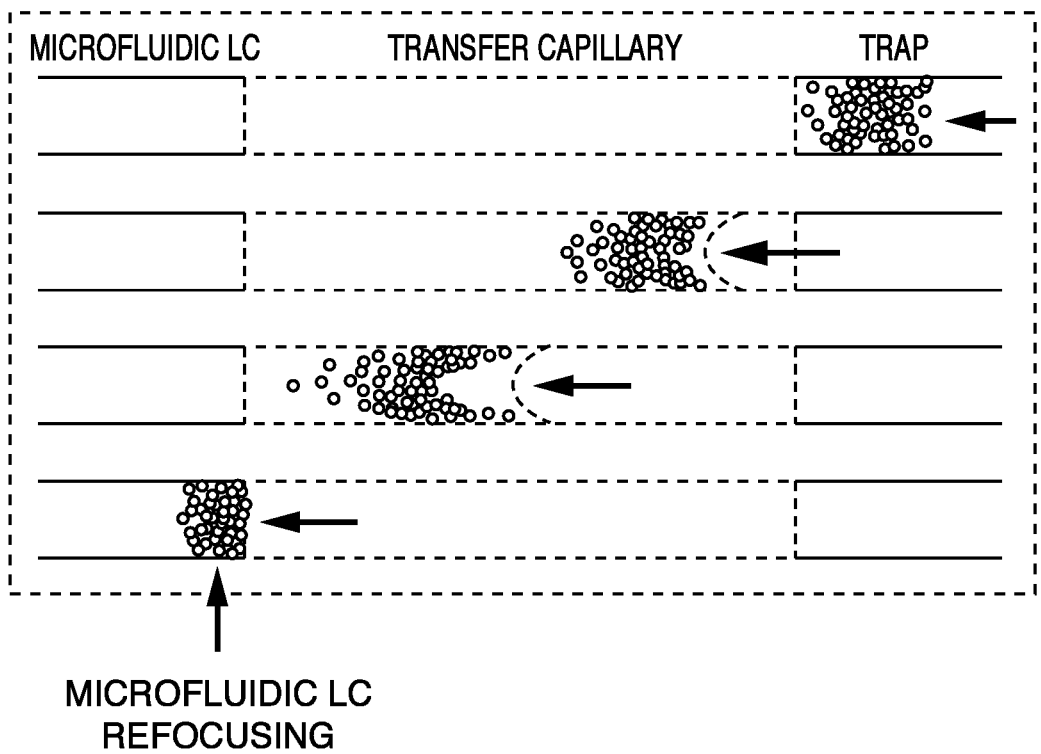
Figure 5A:
FIGS. 5A-5D show the packing configuration for the system.
Figure 5B:
Figure 5C:
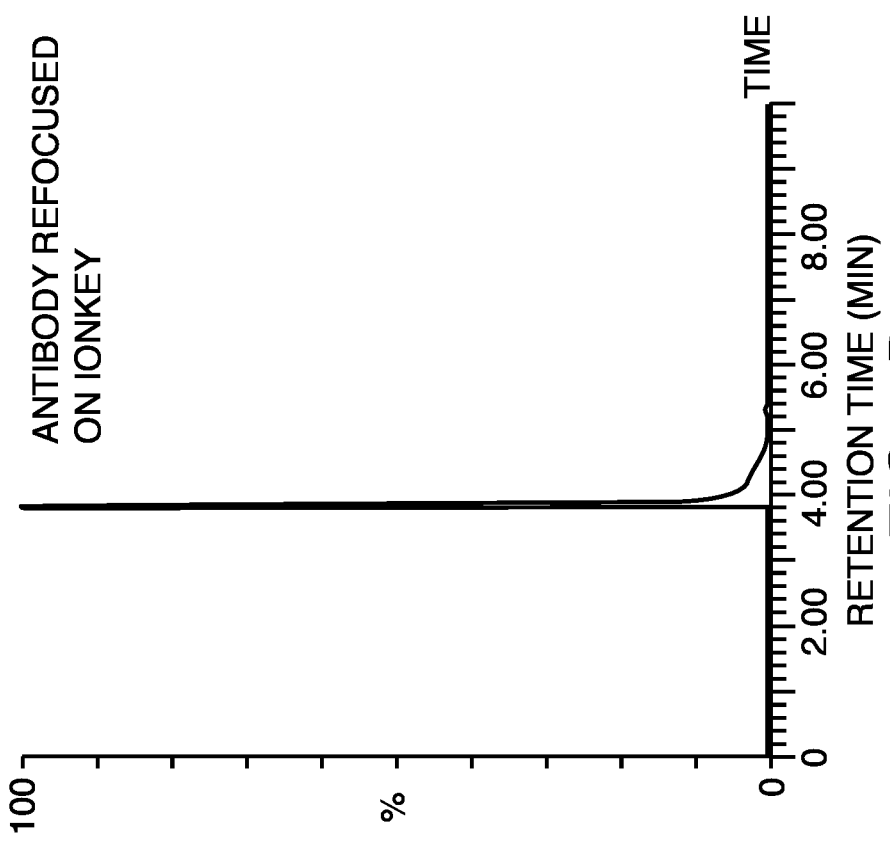
Figure 5D:
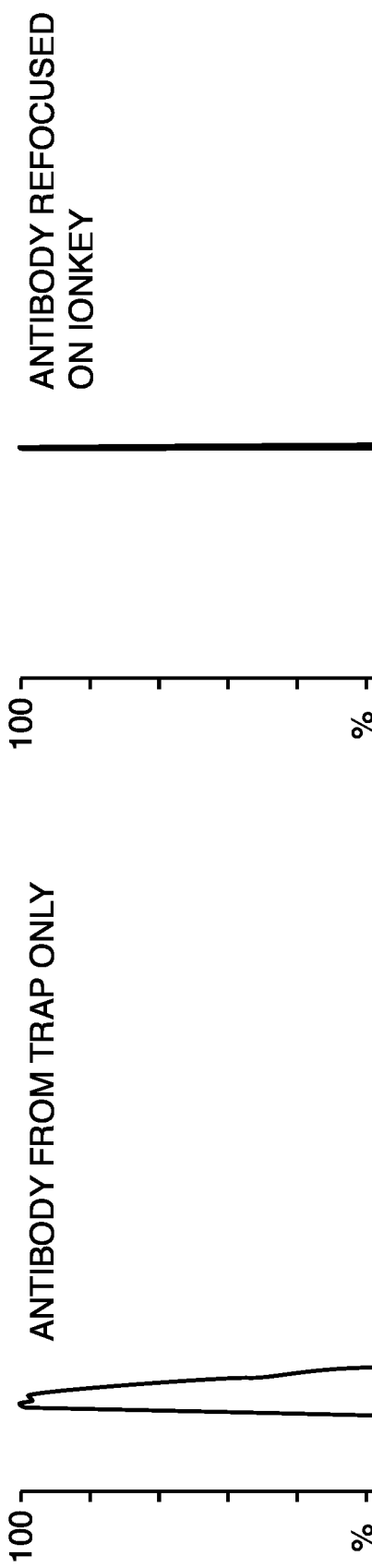

Correctly matching the sorbent in both dimensions of a multi-dimensional LC separation is a very important consideration for micro and nanoscale dimensions. Ensuring that the trap chemistry (first dimension) is slightly less retentive than the microfluidic LC chemistry (second dimension) will enable analyte refocusing between dimensions. This refocusing between first and second dimension is illustrated in FIG. 4. The process involves the analyte eluting from the trap, broadening via parabolic band broadening in the transfer capillary, and then refocusing on the second dimension. The extent of refocusing depends on the relative retentivity difference between the two stationary phases of each dimension. It was demonstrated the relative refocusing that occurs between a phenyl trap and a C4 BEH microfluidic device. The first experiment demonstrated the peak width that occurs from the phenyl trap itself FIGS. 5A and 5B. The path length included the transfer tubing and an open tubular, unpacked, microfluidic device (FIG. 5A). Following this experiment the open tubular microfluidic device was replaced with a packed particle C4-BEH microfluidic device (FIG. 5B). FIG. 5D demonstrates the refocusing between the phenyl trap coupled to the packed particle C4-BEH microfluidic device. Peak width at 10% peak height was 2.38+−0.05 s (n=5, 2% RSD) for the 2D system, as compared to 132 s (n=5, 6% RSD) for the trap alone (FIG. 5C). The trap load and elution were maintained equivalent in both configurations. Removing the trapping column and direct injecting onto the microfluidic device yields a peak width of 2.4+−0.08 s (n=5, 2% RSD), which was statistically equivalent to the trapping configuration, suggesting that precolumn band broadening in trapping and transfer is eliminated upon refocusing on the microfluidic device.

Figure 6C:
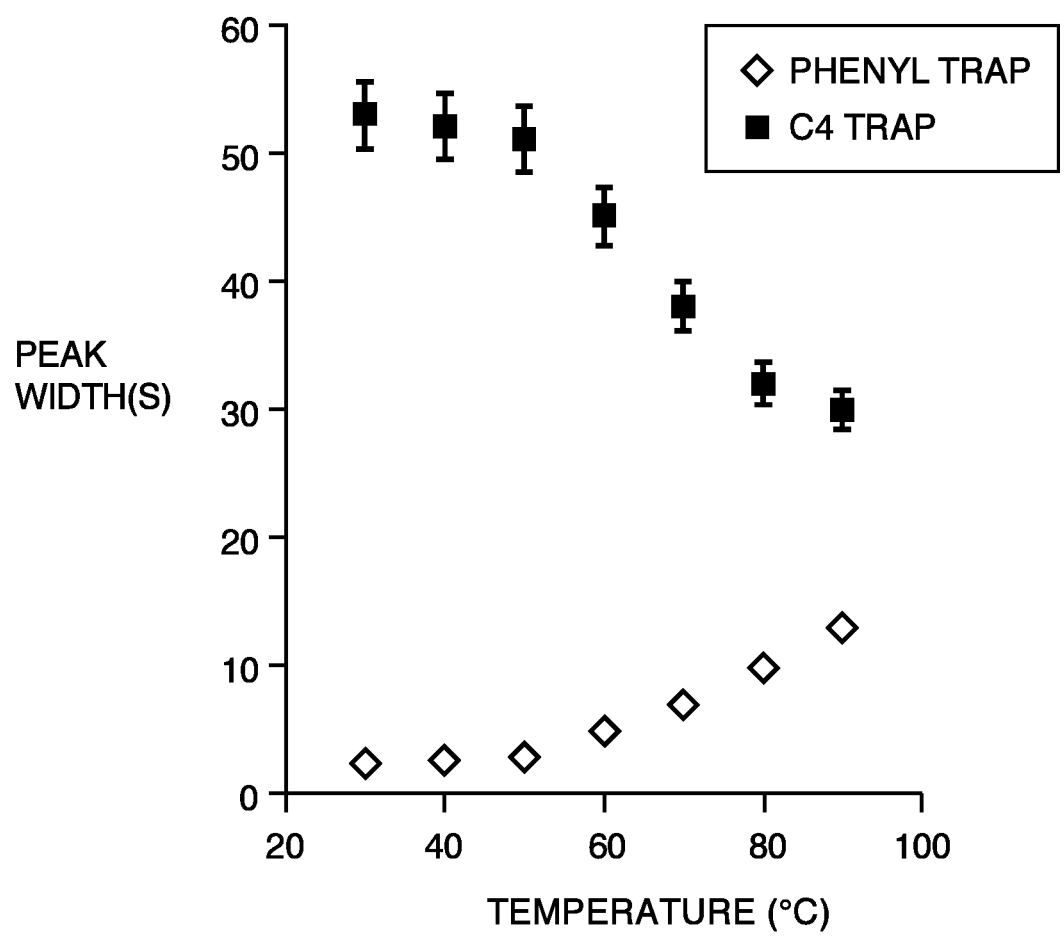

There are currently a limited number of chemistry sorbents that pair with C4 reversed phase sorbent. Many of the sorbents that have a lower retentivity of C4 are designed primarily for hydrophilic polar small molecules. The two chemistries that were identified as acceptable retentivity pairing with RP C4 were a HIC stationary phase particle (TSKgel Phenyl-5PW, TOSOH) and the X-Bridge C4 particle (Waters). These two traps paired with a BEH-C4 microfluidic device differed in the relative retentivity and peak shape. FIG. 6 demonstrates the relative difference between the optimized C4 X-bridge trap (FIG. 6B) and the optimized phenyl trap (FIG. 6A). The lower retentivity of the phenyl desalting particle afforded greater refocusing capability, and resulted in longer retention time and lower band width. Since the X-Bridge C4 trap combined with the BEH C4 microfluidic LC had a much lower differential retentivity there was less refocusing, causing the peak to elute earlier in the gradient with greater peak width. This suggests that not all of the pre-column band broadening that occurs in both the trap and transfer tubings is eliminated upon refocusing. Testing the traps with respect to peak width versus temperature demonstrated that at elevated temperatures the phenyl trap generated greater breakthrough and peak width of the intact antibodies, affording to its lower retentivity shown in FIG. 6C. The opposite was true for increases in temperature for the higher retentivity X-bridge C4 trap, that yielded better peak shape due to improved refocusing between the two stationary phases.

ESI Spray Characteristics, LOD and Quantitative Linear Dynamic Range

The electrospray of intact proteins was analyzed at a series of different scales ranging from 150 micron ID with flow rates of 5 uL/min to 2.1 mm ID with flow rates of 600 uL/min. For identical MS inlet conditions two distinct charge state distributions were observed between the high flow rate 2.1 mm column combined with a desolvation gas ESI probe and the low flow 150 micron column coupled to a purely ESI emitter. FIGS. 7A and 7B demonstrate the charge state distribution that was obtained for a standard glycosylated IgG between these two conditions. Two general phenomena were present: 1) the charge state distribution was narrower, and 2) the average charge state was shifted to higher charge for microflow as compared to standard flow. It is thought that since the distribution of droplet sizes is narrower in low flow ESI, that this is imparted to the charge state distributions of the antibodies. The shifting of the charge state distribution for antibodies at lower ID ESI emitters and lower flows is also thought to be a result of the higher charged droplets that are formed in electrospray.

Figure 7C:
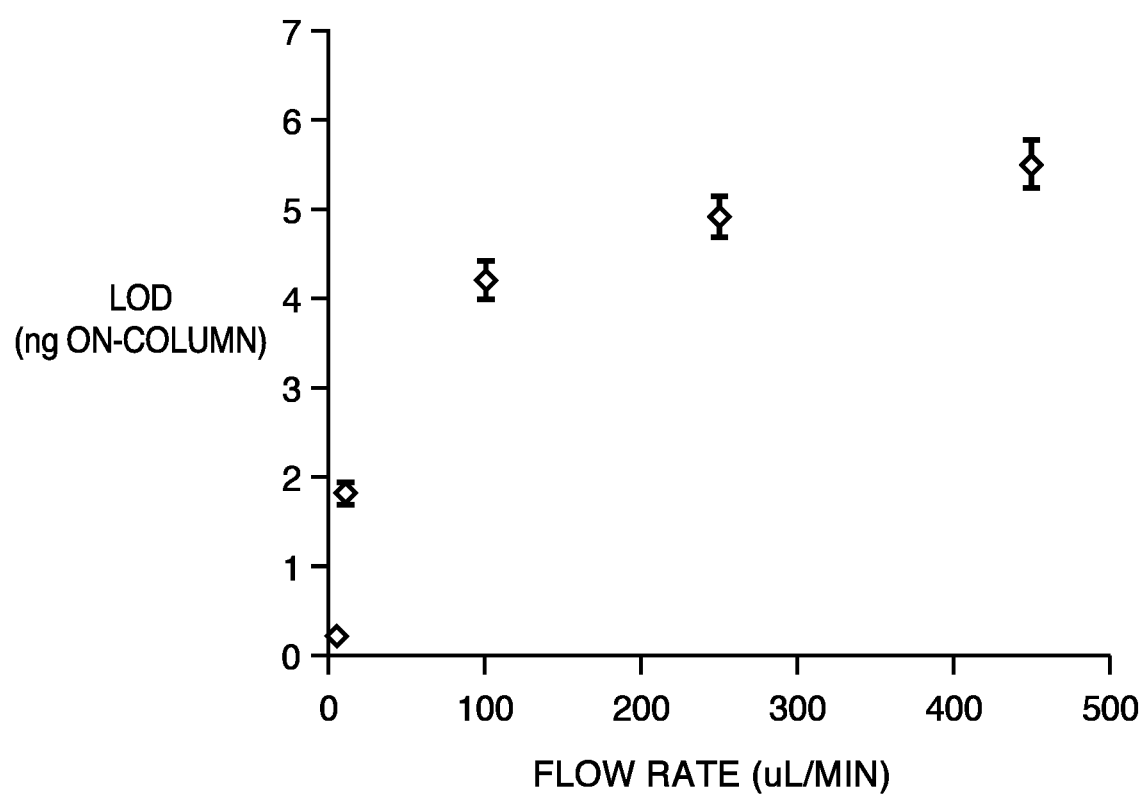
FIG. 7 shows A & B: dependency on the charge state distribution on flow rate of LC for low flow and high flow conditions; C: limits of detection as compared to flow rate for intact mAb; and D & E: linearity of quantitative analysis between 2.1 mm scale and microfluidic devices.

The limits of detection were also improved for intact antibodies at low flow over conventional flow. Measurements of flow rate versus S:N for a standard IgG was performed for high and low flows and is shown in FIG. 7C. The exponential increase in sensitivity as the scale of the chromatography is decreased, in combination with the decrease of flow rate is a result of the improved ionization efficiency present at low flow ESI. This ionization efficiency is a resultant of smaller droplet sizes and increased charge per droplet.

Figures 7D, 7E:
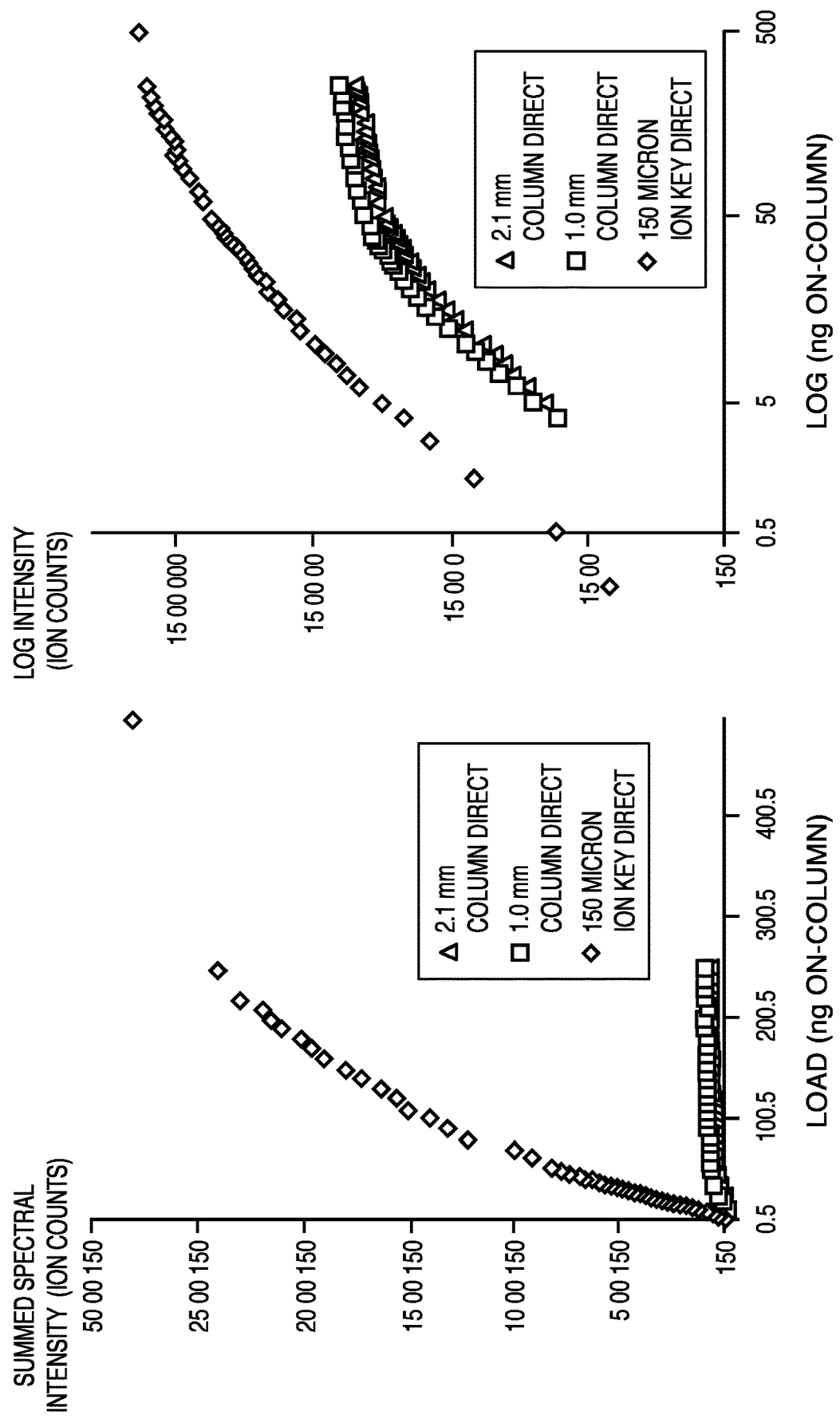

Due to improvements in sensitivity also observed was the extending of the linear dynamic range on 150 micron ID microfluidic, as compared to 2.1 mm standard flow. Although increases in sensitivity were observed, larger dynamic range for microscale ESI over conventional flow ESI was observed, illustrated in FIGS. 7D and 7E. Without being bound to any one particular theory, greater linearity may be due, in part, to improved sensitivity that allows the dynamic range of the ESI and MS detector to reach a lower level, while high end response starts to deviate from linearity at similar loading on-column.

Figure 8:
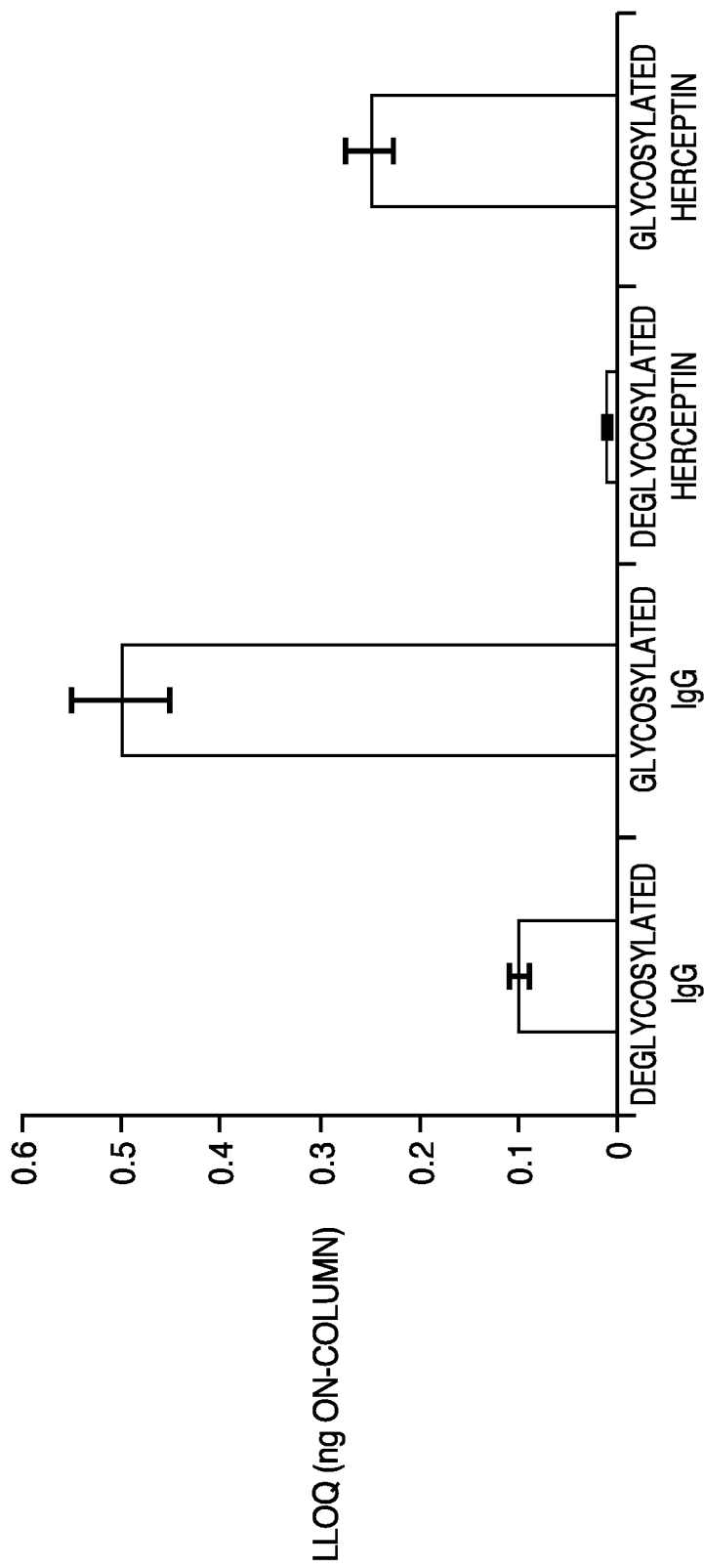
FIG. 8 shows limits of detection and sensitivity for glycosylated and non-deglycosylated IgG and Herceptin using the microfluidic device.
Figure 9C:
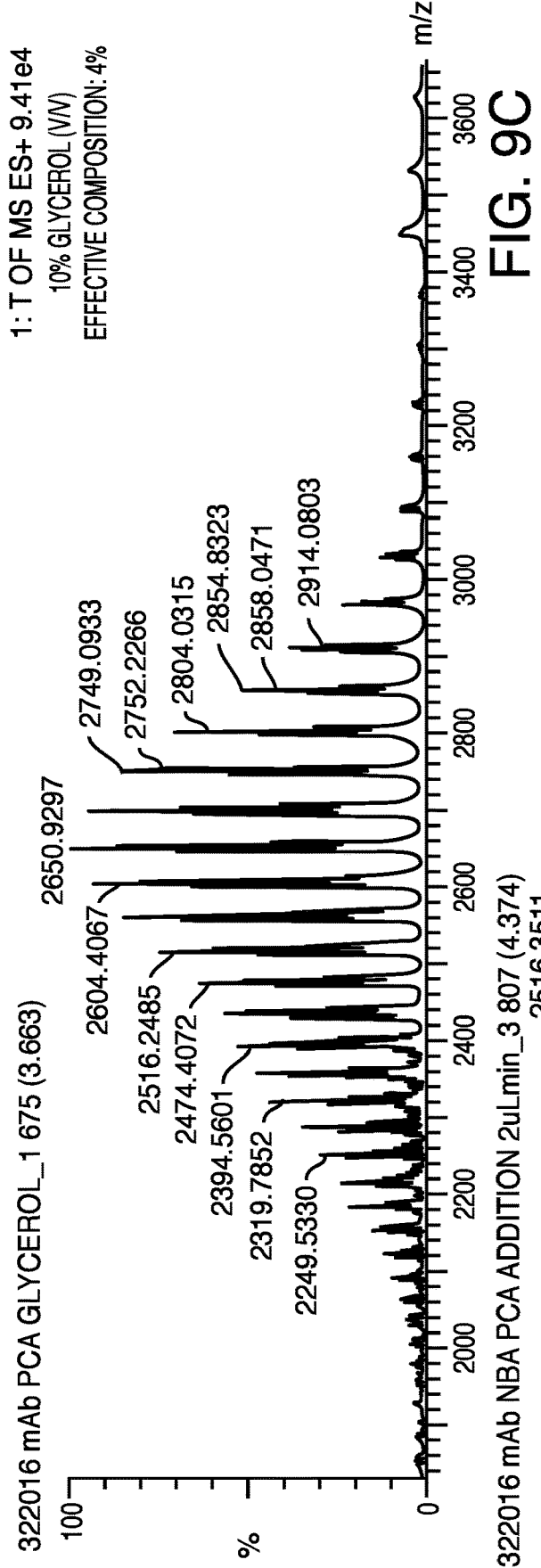
Figure 9D:
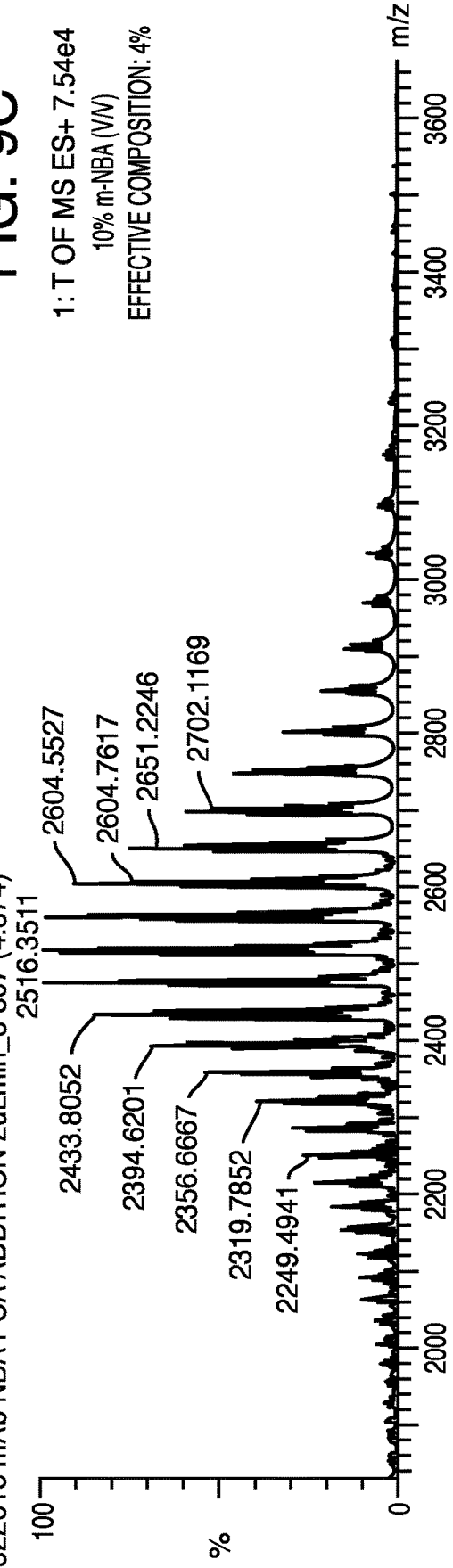

Charge splitting associated with ever more complex antibodies are also thought to heavily impact the resulting S:N ratios. For example, if a deglycosylated antibody is represented as having a signal of 100%, glycosylation will further split that ion current across the population of glycoforms. If four glycoforms of equal intensity were added, the theoretical split of the ion current will form 4 equivalent intensities that are 25% of the height relative to the deglycosylated antibody. A difference of 75-95% in S:N LOD was observed between glycosylated and deglycosylated IgG antibodies that have 4 major glycoforms. FIG. 8 illustrates the difference in signal to noise for glycosylated and deglycosylated IgG standard, in addition to comparison between Herceptin that was glycosylated and deglycosylated.

Supercharging and Decharging using Post Column Addition

Figure 10A:
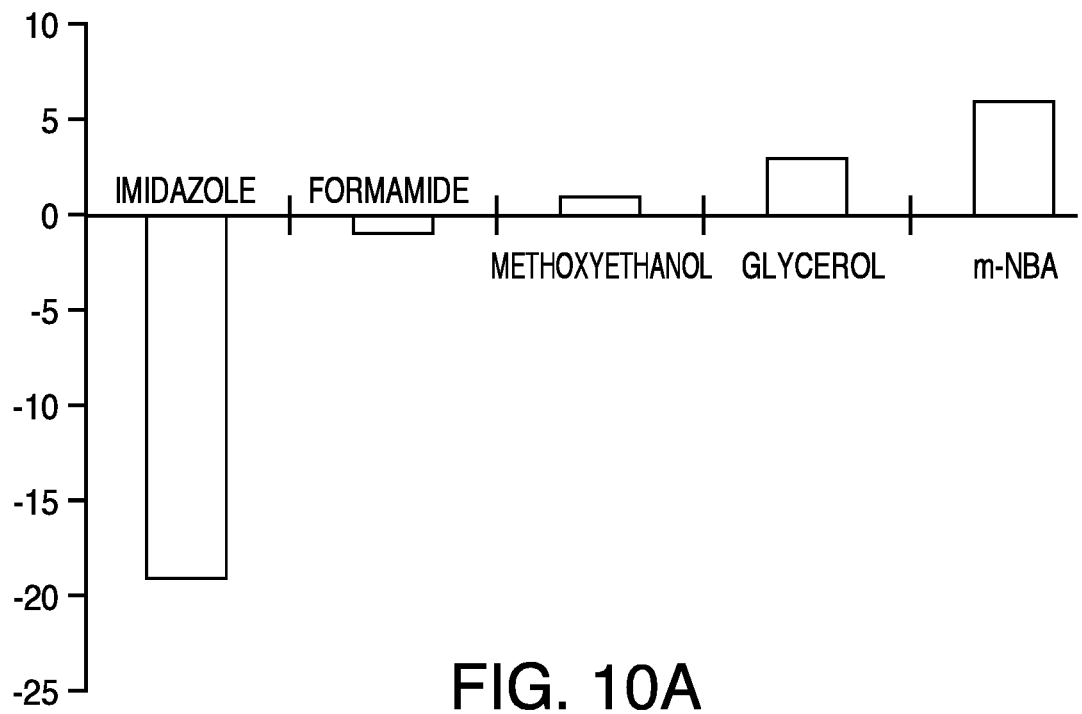
FIG. 10 shows A: the average charge state shifts for the superchargers screened in this study; and B: increases in signal to noise for the supercharging and decharging experiments.
Figure 10B:
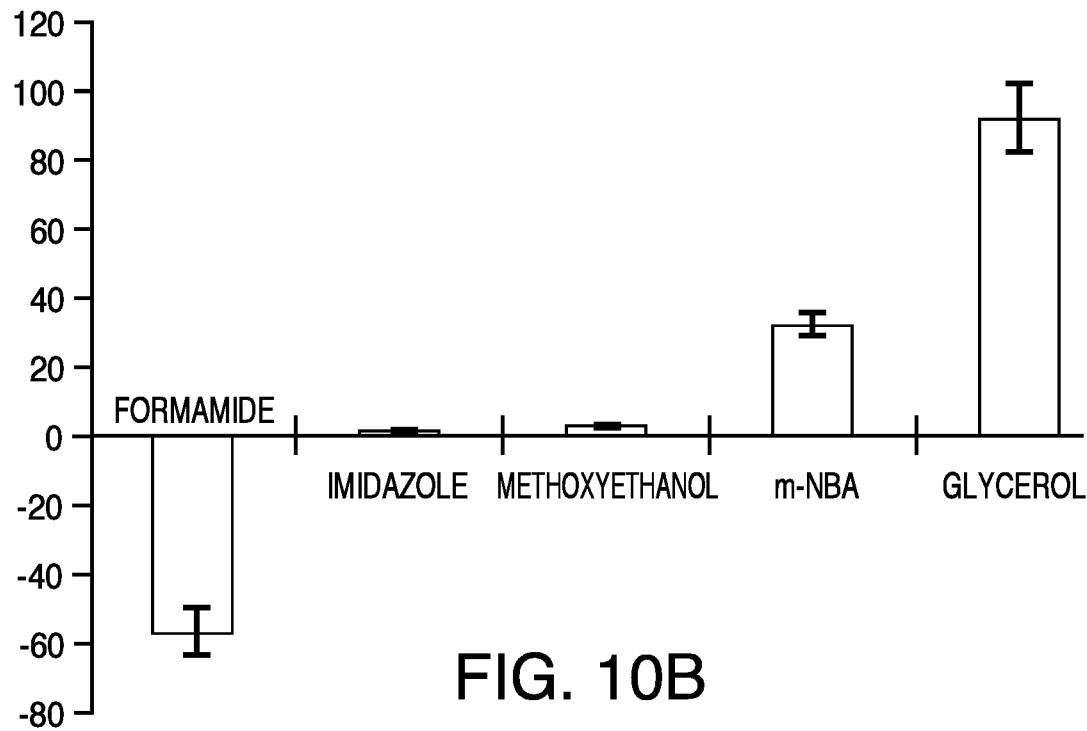

In addition to the normal mechanisms of ESI spray described above, also investigated were supercharging and decharging of antibodies and antibody drug conjugates using the post column addition microfluidic device shown in FIG. 3A. This device enabled us to mix the LC eluent with the supercharging or decharging reagent within the emitter tip. Diffusional mixing within the emitter tip and spray droplets was sufficient to perform supercharging and decharging. FIGS. 9A-9D illustrate the optimal supercharging profiles obtained using a series of supercharging reagents. Glycoform resolution was retained in this experiment across all supercharging reagents, without any major adduct formation. The average charge state deviation from the antibody or antibody drug conjugate is shown in FIG. 10A. Both m-NBA and glycerol provided the greatest shift in charge state, however glycerol provided the best signal enhancement, yielding 89% increase in S:N (FIG. 10B). Given Eq. 3 (presented above), the increase in signal to noise for +6 charge shift state and +4 charge shift state for m-NBA and glycerol respectively was calculated. The theoretical enhancements for both m-NBA and glycerol, based on their supercharging capabilities alone, was calculated to be 75 and 84%, respectively. The difference between this theoretical enhancement in S:N and what was actually observed were due in part to variances between chemical noise present for these experiments.

Figure 11E:
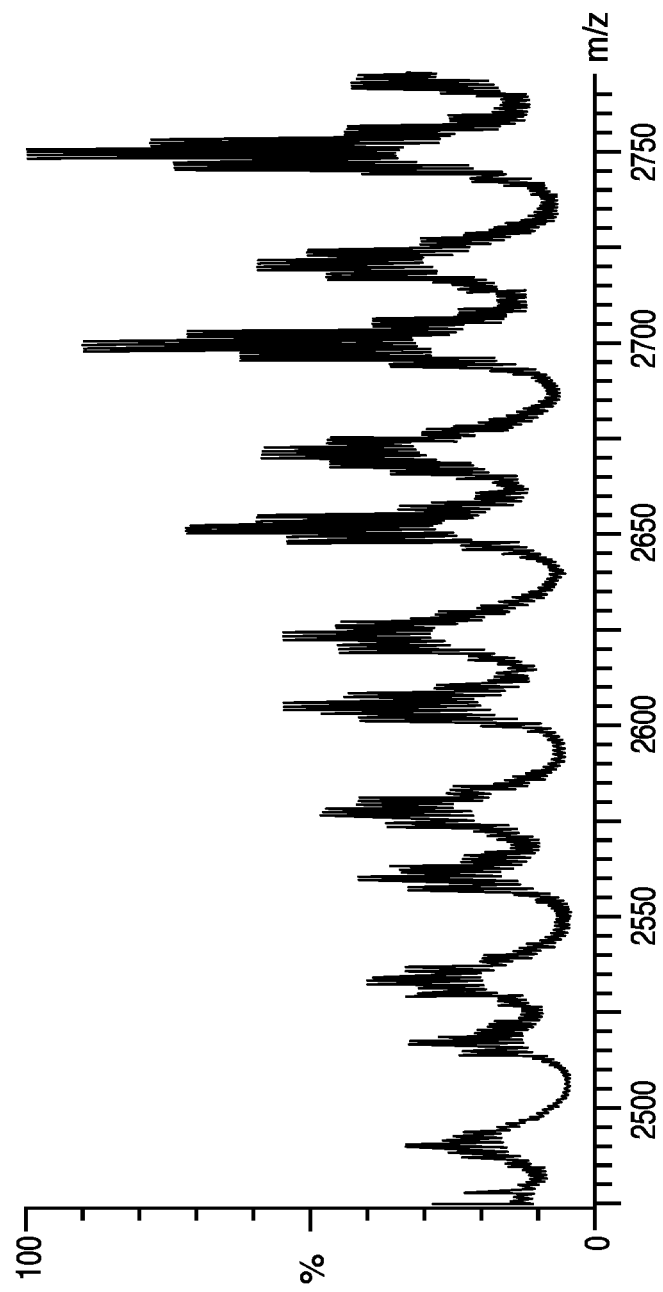
FIG. 11 shows A and B: the effect of decharging mAb using imidazole added post column; and C, D, and E: the functionality of deconvoluting multiple antibodies using the improved charge state spacings.

In addition to supercharging it is possible to also decharge, or charge strip, the antibody in an attempt to improve charge state resolution. In this study imidazole was utilized to shift the charge state by increasing the pH of the LC eluent within the ESI emitter. FIGS. 11A and 11B illustrate the effect of decharging a standard IgG using imidazole PCA addition. The process shifted the CSD by −19 charges, which yielded an increase in charge state spacing by 50%. Such a process affords more spectral space to process complex mAb's and ADC where charge states could overlap. To further test this assumption, two antibodies were added, Silumab and the Waters standard IgG, which coeluted in the chromatograph. FIGS. 11C, 11D, and 11E shows the ability of decharging to better resolve the charge states of two antibodies that are overlapping without decharging, and consequently resolved when decharging is present. The additional charge state spacing available with this decharging experiment enables baseline resolution between the CSD of both Silumab and the Waters standard IgG. This process further simplifies deconvolution and identification of zero charge masses.

Conclusions:

A two dimensional microfluidic device capable of performing supercharging and decharging experimentation in a robust configuration was demonstrated. Chemistry pairing between the phenyl trap and the C4 microfluidic demonstrated excellent refocusing capabilities, and yields modularity replacement between trap and microfluidic LC components. This type of sample "pre-treatment" and instrumental modularity should be an increasingly popular theme for microfluidic devices designed for repetitive analysis of 1,000's of samples. Microflow ESI was also demonstrated to shift the charge state distribution to higher charge and narrower distribution widths relative to high flow ESI. This characteristic of microflow is responsible for the 15× improvement in sensitivity over high flow ESI. The increases in sensitivity also afford increases in linearity over larger scale systems, where higher loads limit both chromatographic performance and ESI spray efficiency due to aggregation. Sensitivity is also dependent upon the complexity of the antibody, as glycans can further split charge states and broaden chromatographic performance which hinders sensitivity. Supercharging was demonstrated here to further improve sensitivity on top of what is already achievable using microflow ESI with glycerol added post column. Alternatively, discharging experiments using imidazole affords greater charge state spacings and yield improvements in analysis of complex antibodies that coelute in the LC.

What is claimed is:

1. A method for analyzing the components of a biological mixture, the method comprising:
    (i) providing a sample comprising one or more of intact antibodies or fragments thereof, antibody drug conjugates or subunits thereof, or intact proteins;
    (ii) exposing the sample to a first dimension comprising a trap;
    (iii) exposing the sample to a second dimension comprising a stationary phase;
    (iv) separating the components of the sample;
    (v) establishing a mass to charge ratio of each of the components in the sample;
    (vi) detecting each of the components in the sample, wherein the detecting step is performed prior to exposing the sample to the second dimension; and
    (vii) adding a supercharging reagent to the sample, wherein the supercharging reagent is glycerol.

2. The method of claim 1, wherein ultraviolet (UV) and/or visible light spectroscopy is used to detect each the components in the sample.

3. The method of claim 1, wherein the detecting step is performed between exposing the sample to the first dimension and the second dimension.

4. The method of claim 1, wherein the supercharging reagent is added to the sample using a microflow device.

5. The method of claim 4, wherein the microflow device comprises a capillary based system.

6. The method of claim 1, wherein the method further comprises adding a decharging reagent to the sample.

7. The method of claim 6, wherein the decharging reagent is imidazole.

8. The method of claim 6, wherein the decharging reagent is added to the sample using a microflow device.

9. The method of claim 6, wherein the decharging reagent is added to the sample after exposing the sample to the second dimension.

10. The method of claim 9, wherein the decharging reagent is added to the sample between exposing the sample to the second dimension and establishing a mass to charge ratio of each of the components in the sample.

11. A method for analyzing the components of a biological mixture, the method comprising:
    (i) providing a sample comprising one or more of intact antibodies or fragments thereof, antibody drug conjugates or subunits thereof, or intact proteins;
    (ii) exposing the sample to a first dimension comprising a trap;
    (iii) exposing the sample to a second dimension comprising a stationary phase;
    (iv) separating the components of the sample;
    (v) establishing a mass to charge ratio of each of the components in the sample; and
    (vi) adding a supercharging reagent to the sample, wherein the supercharging reagent is added to the sample after exposing the sample to the second dimension.

12. The method of claim 11, wherein the supercharging reagent is selected from the group consisting of formamide, methoxyethanol, glycerol, and m-nitrobenzyl alcohol (m-NBA).

13. The method of claim 12, wherein the supercharging reagent is glycerol.

14. The method of claim 11, wherein the method further comprises adding a decharging reagent to the sample.

15. The method of claim 14, wherein the decharging reagent is imidazole.

16. A method for analyzing the components of a biological mixture, the method comprising:
    (i) providing a sample comprising one or more of intact antibodies or fragments thereof, antibody drug conjugates or subunits thereof, or intact proteins;
    (ii) exposing the sample to a first dimension comprising a trap;
    (iii) exposing the sample to a second dimension comprising a stationary phase;
    (iv) separating the components of the sample;
    (v) establishing a mass to charge ratio of each of the components in the sample;
    (vi) detecting each of the components in the sample, wherein the detecting step is performed prior to exposing the sample to the second dimension, and
    (vii) adding a supercharging reagent to the sample, wherein the supercharging reagent is added to the sample after exposing the sample to the second dimension.

17. The method of claim 16, wherein the supercharging reagent is added to the sample between exposing the sample to the second dimension and establishing a mass to charge ratio of each of the components in the sample.

* * * * *